US010982155B2

(12) United States Patent
Verma et al.

(10) Patent No.: US 10,982,155 B2
(45) Date of Patent: *Apr. 20, 2021

(54) VISCOSITY REDUCTION OF CRUDE OIL THROUGH STRUCTURE DETERMINATION OF ASPHALTENE MOLECULE

(71) Applicants: NextStream Heavy Oil, LLC, Oklahoma City, OK (US); William Marsh Rice University, Houston, TX (US)

(72) Inventors: Manjusha Verma, Fulshear, TX (US); Pradeep Venkataraman, Houston, TX (US); Sivaram Pradhan, Houston, TX (US); Houman Michael Shammai, Houston, TX (US); Wilbur Edward Billups, Houston, TX (US); Scott Wellington, Bellaire, TX (US)

(73) Assignees: NextStream Heavy Oil, LLC; William Marsh Rice University

( * ) Notice: Subject to any disclaimer, the term of this patent is extended or adjusted under 35 U.S.C. 154(b) by 0 days.

This patent is subject to a terminal disclaimer.

(21) Appl. No.: 16/372,049

(22) Filed: Apr. 1, 2019

(65) Prior Publication Data
US 2020/0032147 A1 Jan. 30, 2020

Related U.S. Application Data

(63) Continuation of application No. 15/367,171, filed on Dec. 1, 2016, now Pat. No. 10,287,510.

(51) Int. Cl.
| | |
|---|---|
| *C10G 11/02* | (2006.01) |
| *G01N 33/28* | (2006.01) |
| *G01N 21/65* | (2006.01) |
| *C10G 47/02* | (2006.01) |
| *C10G 49/02* | (2006.01) |
| *C10G 11/05* | (2006.01) |
| *G01N 21/3577* | (2014.01) |
| *G01N 23/02* | (2006.01) |
| *G01N 24/08* | (2006.01) |
| *G01N 21/35* | (2014.01) |

(52) U.S. Cl.
CPC ............ *C10G 11/02* (2013.01); *C10G 11/05* (2013.01); *C10G 47/02* (2013.01); *C10G 49/02* (2013.01); *G01N 21/3577* (2013.01); *G01N 21/65* (2013.01); *G01N 23/02* (2013.01); *G01N 33/287* (2013.01); *G01N 33/2823* (2013.01); *G01N 33/2858* (2013.01); *C10G 2300/1033* (2013.01); *C10G 2300/1096* (2013.01); *G01N 24/08* (2013.01); *G01N 2021/3595* (2013.01)

(58) Field of Classification Search
CPC ........ C10G 11/02; C10G 47/02; C10G 49/02; C10G 2300/1033; C10G 2300/1096; G01N 21/3577; G01N 21/65; G01N 2021/3595; G01N 24/08; G01N 24/088; G01N 33/2823; G01N 33/287
See application file for complete search history.

(56) References Cited

U.S. PATENT DOCUMENTS

| | | | |
|---|---|---|---|
| 2007/0161039 A1* | 7/2007 | Wagner .................. | C40B 30/08 435/7.1 |
| 2013/0220883 A1 | 8/2013 | Mazyar et al. | |
| 2014/0225607 A1 | 8/2014 | Edwards et al. | |
| 2015/0219614 A1 | 8/2015 | Respini et al. | |

OTHER PUBLICATIONS

Abdallah, et al., "Raman spectrum of asphaltene", Energy Fuels, 2012, 26 (11) 6888-6896.
Abdallah, et al., "Study of Asphaltenes Adsorption on Metallic Surface Using XPS and TOF-SIMS", J. Phys. Chem. C 2008, 112 (48) 18963-18972.
Alemany, et al., "Solid-and Solution-State Nuclear Magnetic Resonance Analyses of Ecuadorian Asphaltenes:, Quantitative . . . ", Energy Fuels 2015, 29, (10), 6317-6329.
Ardakani, J. et al., "A comparative study of ring opening of naphthalene, tetralin and decalin over Mo2C/HY and Pd/HY catalysts", Appl. Catal. 2011, 403, 36-47.
Biswas, P. et al., "Characterization and Activity of ZrO2 Doped SBA-15 Supported NiMo Catalysts for . . . ", Industrial & Engineering Chemistry Research 2011, 50 (13) 7882-789.
Boek, E.S., et al., "Quantitative molecular representation of asphaltenes and molecular dynamics simulation of . . . " Energy Fuels 2009, 23 (3), 1209-1219.
Bouhadda, Y., et al., "Second order Raman spectra of Algerian Hassi-Messaoud asphaltene", Fuel 2008, 87, (15-16), 3481-3482.
Cabrales-Navarro, F.A., et al., "Catalytic Steam Cracking of a Deasphalted Vacuum Residue Using a Ni/K Ultradispersed . . . ", Energy Fuels, 2017, (3), 3121-3131.
Campbell, D.M., et al., "Construction of a molecular representation of a complex feedstock by Monte Carlo and quadrature . . . ", Applied Catalysis A: General 1997, 160 (1) 41-54.
Campbell, J.H., et al., "Gas evolution during oil shale pyrolysis. 1. Nonisothermal rate measurements", Fuel, 1980, 59, 718-726.
Campbell, J.H., et al., "Gas evolution during oil shale pyrolysis. 2. Kinetic and stoichiometric analysis", Fuel 1988, 59, 727-732.
Chakravarty, T., et al., "Computer-Assisted Interpretation of Pyrolysis Mass Spectra of Two Oil Shales and Their Corresponding . . . ", Energy Fuel, 1988, 2, 191-196.

(Continued)

*Primary Examiner* — Renee Robinson
(74) *Attorney, Agent, or Firm* — Bracewell LLP; Constance R. Rhebergen

(57) ABSTRACT

Asphaltene may be effectively broken into smaller molecules by first elucidating the structure of the asphaltene and then developing a catalyst system based on the elucidated structure. The structure may be determined based on a series of analytical techniques including NMR, FTIR, Raman spectroscopy, XPS, and LDI. The most probable structure is determined using computational methods based on quantum mechanics and classical molecular dynamics and the catalyst system is developed for the most probable structure.

20 Claims, 16 Drawing Sheets

(56) References Cited

OTHER PUBLICATIONS

Chen, Y., et al., "The viscosity reduction of nano-keggin-K3PMo12040 in catalytic aquathermolysis of heavy . . . ", Fuel, 2009, 88, 1426-1434.

Choi, J., et al., "Reducibility and toluene hydrogenation activity of nickel catalysts supported on gamma-A1203 and kappa-A1203", Catalysis Science & Tech. 2012, 2 (1) 179-186.

Choudhary, V.R., et al., "Oxidative Conversion of Methane to Syngas over Nickel Supported on Commercial Low Surface Area . . . ", Journal of Catalysis, 1997, 172 (2) 281-293.

Chuan, W., et al., Mechanism for reducing the viscosity of extra heavy oil by aquathermolysis with an amphiphilic catalyst, J. Fuel Chem. Technol., 2010,38 (6) 684-690.

Dejhosseini, M., et al., "Catalytic Cracking Reaction of Heavy Oil in the Presence of Cerium Oxide Nanoparticles in Supercritical Water", Energy Fuels, 2013, 27 (8) 4624-4631.

Diallo, M.S., et al., "Thermodynamic properties of asphaltenes: a predictive approach based on computer assisted . . . " Developments in petroleum science, 2000, 40, 103-124.

Dumanli, A.G., et al., "Co-firing of biomass with coals Part 1. Thermogravimetric kinetic analysis of combustion of fir . . . ", J. Therm Anal. Calorim., 2011, 103, 925-933.

Gabrienko,A., et al., "Chemical Visualization of Asphaltenes Aggregation Processes Studied in Situ with ATR-FTIR Spectroscopic . . . " J. Phys. Chem. C, 2015, 119 (5) 2646-60.

Kewen, L., et al., "Application of Carbon Nanocatalysts in Upgrading Heavy Crude Oil Assisted with Microwave Heating", Nano Lett., 2014, 14, 3002-3008.

Kowalewski, I., et al., "Preliminary results on molecular modeling of asphaltenes using structure elucidation programs in conjunction . . . " Energy Fuels, 1996, 10 (1) 97-107.

Larachi, F., et al., "X-ray Photoelectron Spectroscopy, Photoelectron Energy Loss Spectroscopy, X-ray Excited Auger . . . ", Energy Fuels, 2004, 18 (6) 1744-1756.

Liu, D., et al., "Investigation on Asphaltene Structures during Venezuela Heavy Oil Hydrocracking under Various Hydrogen . . . ", Energy Fuels, 2013, 27 (7) 3692-3698.

Maity, S.K., et al., "Catalytic Aquathermolysis Used for Viscosity Reduction of Heavy Crude Oils: A Review", Energy Fuels, 2010, 24, 2809-2816.

Martin-Martinez, F. J., et al., "Molecular asphaltene models based on Clar sextet theory", RSC Adv., 2015,5 (1) 753-759.

Nassar, N. N., et al., "Metal Oxide Nanoparticles for Asphaltene Adsorption and Oxidation", Energy Fuels, 2011, 25 (3) 1017-1023.

Oliveira, E.C.d.S., et al., "Study of Brazilian asphaltene aggregation by Nuclear Magnetic Resonance spectroscopy", Fuel, 2014, 117 (PA) 146-151.

Pomerantz, A.E., et al., "Two-step laser mass spectometry of asphaltenes", Journal of the American Chemical Society, 2008, 130 (23) 7216-7217.

Rodriguez-Castellon, E., et al., "Nickel and cobalt promoted tungsten and molybdenum sulfide mesoporous catalysts for hydrodesulfurization", Fuel, 2008, 130 (23) 7216-7217.

Ruiz-Morales, Y., et al., "HOM-LUMO gap as an index of molecular size and structure for polycyclic aromatic hydrocarbons . . . ", The J. of Phys. Chem. A 2002, 106 ($) 11283-11308.

Ruiz-Morales, Y., et al., "Polycyclic aromatic hydrocarbons of asphaltenes analyzed by molecular orbital calculations with optical spectroscopy", 2007, 21 (1) 256-265.

Sabbah, H., et al., "Comparing Laser Desorption/Laser Ionization Mass Spectra of Asphaltenes and Model Compounds", Energy Fuels, 2010, 24, 3589-3594.

Sabbah, H., et al., "Laser Desorption Single-Photon Ionization of Asphaltenes: Mass Range, Compound Sensitivity, and Matrix Effects", Energy Fuels, 2012, 26 (6) 3521-3526.

Schacht, P., et al., "Upgrading of Heavy Crude Oil with W-Zr Catalyst", Advances in Chemical Engineering and Science 2014, 4, 250-257.

Sheremata, J.M., et al., "Quantitative molecular repsresentation and sequential optimization of Athabasca ashaltenes", Energy Fuels 2004, 18 (5) 1377-1384.

Siddiqui, M.N., "Catalytic pyrolysis of Arab Heavy residue and effects on the chemistry of asphaltene", Journal of Analytical and Applied Pyrolysis 2010, 89, (2) 278-285.

Soultanidis, N., et al., "Relating n-Pentane Isomerization Activity to the Tungsten Service . . . ", J. of the American Chem. Society 2010, 132, (38), 13462-13471.

Stecks S. J., et al., "Mass Spectrophotometric Volatilization studies of "Symp. on High Temperature and Rapid Heating Reactions of Fuels, Div. Fuel Chem., ACH, Chicago 1970.

Tuinstra, F., et al., Raman Spectrum of Graphite, Journal of Chemical physics 1970, 53 (3) 1126-1130.

Usui, K., et al., "Catalytic hydrocracking of petroleum-derived asphaltenes by transition metal-loaded zeolite catalysts", Fuel,2004, 83 (14-15) 1899-1906.

Venkataraman, P., et al., "Molecular Insights into Glass Transition in Condensed Core Asphaltenes", Energy Fuels, 2017, 31 (2) 1182-1192.

Verma,Manjusha, et al., "Poster", presented at ACS Conference, Denver, CO, Mar. 22-26, 2015.

Vicerich, M.A., et al., "Influence of Na content on the catalytic properties of Pt-Ir/A1203 catalysts for selective ring opening of decalin", Appl. Catal., 2014, 480, 42-49.

Wang S., et al., "Study of asphaltene adsorption on kaolinite by X-ray photoelectron spectroscopy and time-of-flight secondary ion . . . ", Energy Fuels 2013, 27 (5) 2465-2473.

Wang, H., et al., "Supporting Tungsten Oxide on Zirconia by dydrothermal and Impregnation Methods and its use as a Catalyst to Reduce . . . " Energy Fuels 2012, 26 (11) 6518-6527.

Zhao, H., et al., "Kinetics and selectivity of asphaltene hydrocracking", Fuel, 2011, 90 (5) 1900-1906.

Zhao, H., et al., "Thermal characteristics of bitumen pyrolysis", J. Therm Anal. Calorim, 2012, 107, 541-547.

Zhao, Y.X., et al., "Kinetics of asphaltene thermal cracking and catalytic hydrocracking", Fuel Processing Technology, 2011, 92 (5) 977-982.

Zhou, W., et al., "Identification of active Zr-W0x clusters on a Zr02 support for solid acid catalysts", Nature Chemistry, 2009, 1 (9) 722-728.

3rd Canadian Office Action for 2,987,185 dated Jun. 18, 2020, 4 pages.

Machin et al., "Theoretical study of catalytic steam cracking on a asphaltene model molecule," Journal of Molecular Catalysis A: Chemical, vol. 227, Dec. 8, 2004: pp. 223-229.

Badran et al., "Theoretical and thermogravimetric study on the thermo-oxidative decomposition of Quinolin-65 as an asphaltene model molecule," RSC Adv., vol. 6, Jun. 2, 2016: pp. 54418-54430.

Montoya et al., "Kinetics and mechanisms of the catalytic thermal cracking of asphaltenes adsorbed on supported nanopartickles," Pet. Sci., vol. 13, Jul. 1, 2016: pp. 561-571.

Coelho et al., "Characterization of Functional Groups of Asphaltenes in Vacuum Residues Using Molecular Modelling and FTIR Techniques," Petroleum Science and Technology, vol. 25, 2007: pp. 41-54.

\* cited by examiner

VISCOSITY REDUCTION OF CRUDE OIL THROUGH STRUCTURE DETERMINATION OF ASPHALTENE MOLECULE

FIELD

The disclosure relates to a method of catalytically breaking asphaltene macromolecules in a fluid into smaller molecules by first elucidating the structure of the asphaltene macromolecules and then developing a suitable catalyst system based on the elucidated structure.

BACKGROUND

Heavy crude oil from subterranean hydrocarbon reservoirs typically has four fractions: saturates (saturated hydrocarbons), aromatics, resins and asphaltene macromolecules. The high viscosity of heavy crude oil is due, at least partially, to the presence of the asphaltenes. Asphaltenes are further known to adversely impact the viscoelasticity and flow behavior of crude oil.

Asphaltenes also are known to cause operational and safety issues with both hydrocarbon production and processing. For example, they are known to have deleterious effects on the extraction of oil. For instance, asphaltenes are generally stable in bulk oil at relatively high pressures and tend to precipitate at lower pressure or onset pressure. As reservoir pressure decreases and drops below the onset pressure during hydrocarbon production, asphaltenes precipitate and the precipitates block production routes and tubing.

Asphaltene precipitates are further known to flocculate and form deposits in the pores of the formation, coat boreholes and solidify in downhole equipment. Wells with excessive asphaltene deposition may incur high remediation costs but, more importantly, are exposed to levels of formation damage that can greatly shorten the productive life of the well.

In the past, much effort has been undertaken in order to decrease the viscosity of heavy oil and to increase the flow of hydrocarbons from the well by minimizing the precipitation of asphaltenes. Such efforts have been focused on determining an effective catalyst for breaking the bonds of the asphaltenes. However, catalyst selection has not been totally effective. This is attributable, in part, to the fact that catalyst selection has only been based on the activity, selectivity, ease of regeneration and mechanical strength of the catalyst under defined cracking operations.

Improved methods for decreasing the viscosity of heavy oil and to break down asphaltenes are therefore desired.

It should be understood that the above-described discussion is provided for illustrative purposes only and is not intended to limit the scope or subject matter of the appended claims or those of any related patent application or patent. Thus, none of the appended claims or claims of any related application or patent should be limited by the above discussion or construed to address, include or exclude each or any of the above-cited features or disadvantages merely because of the mention thereof herein.

SUMMARY OF THE DISCLOSURE

In an embodiment of the disclosure, a method of catalytically breaking asphaltene macromolecules into smaller molecules with a catalyst system is provided. A target structure of the aromatic core of the asphaltene macromolecules is identified from a collected fluid containing the asphaltene macromolecules. The structure is in part identified by subjecting the asphaltene macromolecules to elemental analysis, Nuclear Magnetic Resonance (NMR) spectra, Raman spectroscopy, FTIR and X-ray photoelectron spectroscopy. Classes of structures with lowest energies are identified using Hartree-Fock method. The structure conforming to molecular weight determined by laser desorption ionization experiments is selected. The presence of one or more aliphatic groups and one or more functional groups within the asphaltene macromolecules is determined by FTIR, X-ray photoelectron spectroscopy and NMR. The probability of a molecular structure from the predicted structures is then approximated by applying Hartree-Fock method and molecular dynamic simulations to the potential structures. The structure having the lowest sum energy of conformational energy and isomerization energy is identified. A catalyst system is then developed from a catalyst inventory capable of breaking the bonds of the structure having the lowest sum energy. The asphaltene macromolecules are then broken down into smaller molecules with the developed catalyst system.

In another embodiment of the disclosure, a method of catalytically breaking down an asphaltene macromolecule is provided. In this method, one or more target structures of the aromatic core of the asphaltene macromolecule may be identified from elemental analysis, NMR spectra, Raman spectroscopy, FTIR and X-ray photoelectron spectroscopy of the asphaltene macromolecule in the fluid sample. Heteroatoms in the asphaltene macromolecule are determined by elemental analysis. The free energy of the one or more target structures is determined using Hartree-Fock method. Aliphatic chains and functional groups of the asphaltene sample may be identified by FTIR, X-ray photoelectron spectroscopy and NMR of the asphaltene macromolecule in the fluid sample. Probable structures of the asphaltene macromolecule may be determined by geometry optimization using Hartree-Fock method and 6-31G* basis set. A catalyst system capable of breaking down the probable structure of asphaltene may be developed from a catalyst inventory. The asphaltene macromolecule may then be broken down in the presence of the catalyst system.

In another embodiment, a method of catalytically breaking down asphaltene macromolecules is provided wherein the probable molecular structure of the aromatic core of an asphaltene macromolecule may be determined by ascertaining the amount of heteroatoms in the asphaltene sample, the functional groups in the asphaltene sample, the degree of aromaticity in the asphaltene sample, the size of the aromatic core of the asphaltene sample, the acid-base profile of the asphaltene sample, and the molecular weight of the asphaltene sample. A catalyst capable of breaking chemical bonds of the asphaltene sample at target sites is selected based on the structure derived using Hartree-Fock method and elemental analysis, NMR spectra, Raman spectroscopy and X-ray photoelectron spectroscopy as well as Laser Desorption/Ionization Mass spectroscopy for molecular weight determination. The asphaltene macromolecules are then heated in the presence of the catalyst to break down the asphaltene macromolecules into fragments of lower molecular weight.

In another embodiment of the disclosure, a method of catalytically breaking down asphaltene macromolecules is provided wherein a fluid sample is first collected containing the asphaltene macromolecules. Potential structures of the aromatic core of the asphaltene macromolecules are identified by subjecting the asphaltene to a variety of analyses. The percent of carbon, hydrogen, nitrogen, oxygen, sulfur, nickel and vanadium in the asphaltene macromolecule as well as the empirical formula of the asphaltene macromolecule may be determined by elemental analysis. (Elemental analysis of the asphaltene macromolecule may further be instructive of the architecture of the aromatic core.) The asphaltene sample may also be subjected to X-ray photoelectron spectroscopy to determine the functional groups in the aromatic core of the asphaltene. The presence of pyridine, pyrrole, sulfoxide and thiophene in the asphaltene and the molar ratios of pyridine, pyrrole, sulfoxide and thiophene in the sample may also be determined from such spectroscopy. The aromatic core size of the sample and the number of aromatic rings in the asphaltene may be ascertained from Raman spectroscopy. Chemical bonds in the asphaltene may be determined from absorption bands in a Fourier Transform Infrared analysis. The aromatic content, aliphatic content and side chain content of the asphaltene may be determined from solid state nuclear magnetic resonance $^1H$ and $^{13}C$ (NMR) wherein the asphaltene sample is spun at its magic angle with respect to the direction of the magnetic field. The asphaltene sample may be subjected to Distortionless Enhancement by Polarization Transfer and, in conjunction with $^{13}C$, the presence of —$CH_3$, —$CH_2$ and —CH in the sample determined. The asphaltene sample may be subjected to heteronuclear single quantum correlation and chains of the asphaltene sample assessed. The asphaltene sample may be subjected to Laser Desorption/Ionization Molecular Weight Determination (LDI) and its molecular weight distribution determined. Alternative molecular structures of the aromatic core may be determined based on a combination of these analytical tests. The free energy of the identified potential structures of the aromatic core may then be determined using Hartree-Fock analysis as quantum chemistry modeling. Oxygen, sulfur and/or nitrogen, if present in the macromolecule, may be identified. The structure with lowest energy as well as the structure which matches the LDI (if different from the structure with lowest energy) is identified. The alternative molecular structures of the aromatic core having the lowest energy may then be targeted. The aliphatic and functional groups of the asphaltene sample may be identified from FTIR, X-ray photoelectron spectroscopy and NMR. Probable molecular structures of the asphaltene macromolecules may then be identified using quantum chemistry modeling geometric optimization analysis using Hartree-Fock method and Molecular Dynamics. A catalyst system capable of breaking chemical bonds of the asphaltene macromolecule is then developed based on one or more of the probable molecular structures.

In another embodiment, a method of catalytically breaking down asphaltene macromolecules into smaller molecules is provided. In this embodiment, potential structures of the aromatic core of the asphaltene sample are identified by determining the number of heteroatoms, the functional groups present, the size of the aromatic core, and the molecular weight of the aromatic core. The identified potential structures are then subjected to quantum chemistry modeling and the potential structure of the aromatic core of the asphaltene sample further defined. Aliphatic and functional groups of the asphaltene sample are identified by FTIR, X-ray photoelectron spectroscopy and NMR. Alternative molecular structures of the asphaltene macromolecules are then further identified based on the identified aliphatic and functional groups of the asphaltene sample and quantum chemistry modeling. A catalyst system is then developed starting with a known catalyst inventory; the developed catalyst system is capable of breaking chemical bonds of the identified molecular structure of the asphaltene. The asphaltene may then be broken down in the presence of the catalyst system.

In another embodiment of the disclosure, a method of breaking the bonds of an asphaltene macromolecule with a catalyst system is provided. In this method, potential structures of the aromatic core of the asphaltene macromolecule are identified by subjecting the asphaltene to elemental analysis, NMR spectra, Raman spectroscopy and X-ray photoelectron spectroscopy. The free energy of the potential structures is then determined using the Hartree-Fock method. Aliphatic and functional groups of the asphaltene macromolecules are then determined by FTIR, X-ray photoelectron spectroscopy and NMR. One or more alternative structures of the asphaltene macromolecules are then determined based on the identification of the aliphatic and functional groups and the potential structure(s) of the aromatic core by applying Hartree-Fock method and determining the free energy of each of the alternative structures. The structure of lowest free energy is selected as the structural formula of the asphaltene macromolecules. A catalyst system is then developed based on the probable structure of low free energy. The asphaltene macromolecules are then broken down in the presence of the catalyst system.

BRIEF DESCRIPTION OF THE DRAWINGS

The following figures are part of the present specification, included to demonstrate certain aspects of various embodiments of this disclosure and referenced in the detailed description herein.

DETAILED DESCRIPTION

Figure 1:
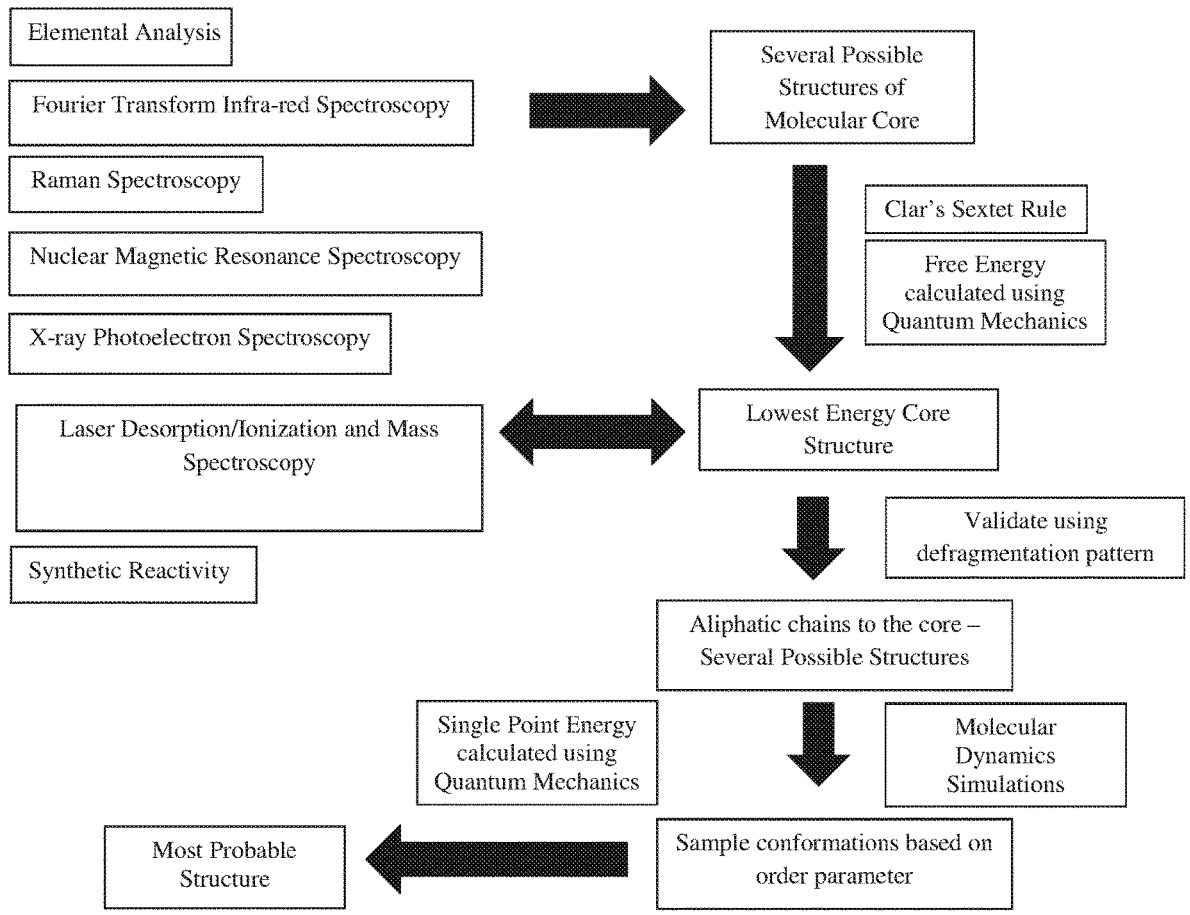
FIG. 1 represents an exemplary pathway for predicting the average structure of an asphaltene.

Characteristics and advantages of the present disclosure and additional features and benefits will be readily apparent to those skilled in the art upon consideration of the following detailed description of exemplary embodiments of the present disclosure and referring to the accompanying figures. It should be understood that the description herein and appended drawings, being of exemplary embodiments, are not intended to limit the claims of this patent or any patent or patent application claiming priority hereto. On the contrary, the intention is to cover all modifications, equivalents and alternatives falling within the spirit and scope of the claims. Many changes may be made to the particular embodiments and details disclosed herein without departing from such spirit and scope.

The terms "including" and "comprising" are used herein and in the appended claims in an open-ended fashion, and thus should be interpreted to mean "including, but not limited to." Further, reference herein and in the appended claims to components and aspects in a singular tense does not necessarily limit the disclosure or appended claims to only one such aspect, but should be interpreted generally to mean one or more, as may be suitable and desirable in each particular instance.

The disclosure relates to a method of identifying the structure of asphaltene macromolecules in a fluid and development of a catalyst system capable of breaking down the identified structure into smaller molecules. The larger macromolecules are broken down by breaking carbon carbon bonds, carbon sulfur bonds, carbon oxygen bonds and carbon hydrogen bonds in the macromolecules. The breaking of such bonds reduces the viscosity of the fluid containing the asphaltene macromolecules.

The structure of asphaltene macromolecules is elucidated from quantum modeling applying Hartree-Fock analysis as well as from elemental analysis, NMR spectra, Raman spectroscopy X-ray photoelectron spectroscopy of a sample of the asphaltene.

The most suitable catalyst system for breaking the chemical bonds of the asphaltene macromolecules is then developed and the reaction mechanism for bond breaking determined. Phase behavior and thermodynamic properties of the asphaltenes may further be predicted based on the elucidated structure.

The term "catalyst system" as used herein may include a catalyst selected from a known inventory, a catalyst developed from a known catalyst inventory, a catalyst from a known catalyst inventory combined with one or more promoters or a catalyst developed from a catalyst from a known catalyst inventory combined with one or more promoters.

In an embodiment, the fluid source containing the asphaltene macromolecules may be crude oil. The viscosity of crude oil may be efficiently reduced by developing the most suitable catalyst system for breaking the macromolecules into smaller molecules of lower molecular weight.

In an application, the flow of crude oil downhole may be improved and the recovery of less viscous crude oil enhanced by identifying weaker chemical bonds in the asphaltene macromolecule. Such weaker bonds can be broken at relatively lower temperatures than previously permitted.

It is widely known that the structure of asphaltene is unknown and varies from one fluid source to another. Thus, the structure of asphaltene from one fluid source is different from the structure of asphaltene obtained from another fluid source. The process disclosed herein may be used to identify the most suitable catalyst system for an asphaltene regardless of the source from which the asphaltene has been sampled.

The modeling described herein is premised on the knowledge that asphaltenes primarily consist of polyaromatic hydrocarbons and aliphatic appendages. In addition, asphaltenes found in crude oil may also contain metallic elements such as nickel, vanadium, iron and such heteroatoms as sulfur, nitrogen and oxygen.

The process described herein allows for the design and/or selection of a catalyst system which may specifically target bond types (e.g. C—S, C—C etc.). Since significant improvements to the flow properties of fluids may be attained by altering the content or structure of asphaltenes, the process provides for a more efficient design and selection of catalysts for chemically altering the structure of the asphaltenes.

The structure of an asphaltene may be determined by identifying, within a collected fluid sample of asphaltene, the amount of heteroatoms (such as nitrogen, oxygen and sulfur), the functional groups present (especially carbonyls, hydroxyls and sulfoxides attached to the asphaltene molecule), the degree of aromaticity or the amount of benzene-like rings in the core of the asphaltene molecule), the size of the aromatic core of the asphaltene, the acid-base profile and the molecular weight of the asphaltene sample. All of these properties contribute to the polarity and steric interactions of asphaltene molecules and aggregates of asphaltene molecules and are controlling in the development of the most ideal catalyst system for breaking the asphaltene.

Such factors further are indicative of how asphaltene macromolecules interact on a particular catalyst surface. Surface charge, van der Waals forces and polar interactions between the catalyst surface and asphaltene molecules are prominent driving forces for adsorption of the asphaltene on the catalyst surface. Increasing polarity, through heteroatom content or increased aromaticity, and decreasing steric hindrance (due to peripheral alkane chain in asphaltene molecules) allow asphaltene molecules to interact more favorably with the surface of the catalyst.

The functional groups of the asphaltene allow the adsorption of asphaltene molecules on the catalyst surface by sharing electrons. Functional groups consisting of nitrogen and oxygen heteroatoms, often concentrated in asphaltene molecules, are known to be significant for initiating surface-specific adsorption interactions. Reactivity of asphaltene molecules with a specific catalyst system is therefore dependent on the type of functional groups attached to the asphaltene such as carbonyl, pyrrole, pyridine, thiophene and sulfoxide. Asphaltene molecules having carbonyl groups are further susceptible to either an acidic and or basic catalyst based on reaction conditions.

Further, interaction of the catalyst system with the asphaltene molecule decreases the activation energy of carbon-carbon bond breaking and carbon-hydrogen bond breaking and enhances the reaction rate. Moreover, the catalyst system can decrease the reaction temperature.

The method for determining the structure of asphaltene macromolecules encompasses quantum modeling and a series of analytical techniques such as elemental analysis, nuclear magnetic resonance (NMR), Fourier transform infrared (FTIR), Raman spectroscopy, X-ray photoelectron spectroscopy (XPS), laser desorption/ionization (LDI) and mass spectrometry. In addition, the method explores the synthetic activity of the asphaltene extract. Each of the analytical techniques provides specific structural information which, when combined each other, renders an average structure of any asphaltene extracted from a fluid.

Enhancement of adsorption of the asphaltene molecules onto the surface of the catalyst is dependent on the correct identification of the heteroatoms, the functional group in which the heteroatoms are present and the amount of the functional groups in the asphaltene molecule. It is preferred that the assessment be undertaken in a series of steps though the sequence of the steps may vary.

An exemplary strategy for determining the most probable structure of a sample of asphaltene is illustrated in FIG. 1. The most probable structure may be determined from the elemental content, aromaticity, aromatic core size, element bonding, molecular weight, exfoliation and other reactions and techniques as well as geometry optimization equations and programs.

In the first step, as illustrated in FIG. 1, several possible structures of the aromatic core of the asphaltene are determined. These structures are determined based on data obtained from Elemental Analysis, Fourier Transform Infrared Spectroscopy (FTIR), Raman Spectroscopy, Nuclear Magnetic Resonance Spectroscopy (NMR) and X-ray Photoelectron Spectroscopy (XPS). The possible core structures will have similar stoichiometry and molecular weight. Structures determined to be stable under Clar's sextet theory are selected for further analysis.

The core of the asphaltene, as well as the empirical formula of the asphaltene, may be determined by elemental analysis. Typically, the asphaltene from crude may be extracted using a hydrocarbon solvent, such as pentane or heptane. Elemental analysis may be determinative of the amount of carbon, hydrogen, nitrogen, oxygen, sulfur, nickel and metal, such as vanadium, in the extracted sample. While the percentage of each such element varies from oil collected from one reservoir to another, the average values of such components is reported to be from 76 to 86 wt. % carbon, 7.3-8.5 wt. % hydrogen, 5 to 9 wt. % sulfur, 0.7-1.2 wt. % oxygen, 1.3-1.4 wt. % nitrogen and 0.1-0.2 wt. % of nickel, iron and vanadium. The empirical formula of the extracted asphaltene sample may be determined.

Elemental analysis is useful in identifying further the aliphatic chains of the asphaltene. While elemental analysis may be useful in identifying the aromatic core of the asphaltene, Raman spectroscopy is more instructive. In particular, Raman spectroscopy is useful in determining the size of the aromatic core and the number of aromatic rings in the core.

The aromatic core refers to the aromatic ring structure of the asphaltene which may include a fused aromatic region. The aromatic ring structure may further be referred to as the architecture of the asphaltene. Typically, the architecture of asphaltenes is either rosary, island or a combination of rosary and island. The "island" architecture in asphaltene has been reported to be monomeric (in the molecular weight range of about 500 to 1000 Da) consisting of (on average) a core of about six to seven fused aromatic rings surrounded by several aliphatic groups with some heteroatoms. The "rosary-type" architecture has been reported to consist of individual asphaltene monomers composed of clusters of polycondensed groups consisting of five to seven aromatic rings each connected by short aliphatic side chains, possibly containing polar heteroatom bridges. Rosary-type architecture is normally expected to have less aromatic rings than the island architecture.

Exemplary architectures of the rosary-type and island type of aromatic architecture is shown below as (A) and (B), respectively:

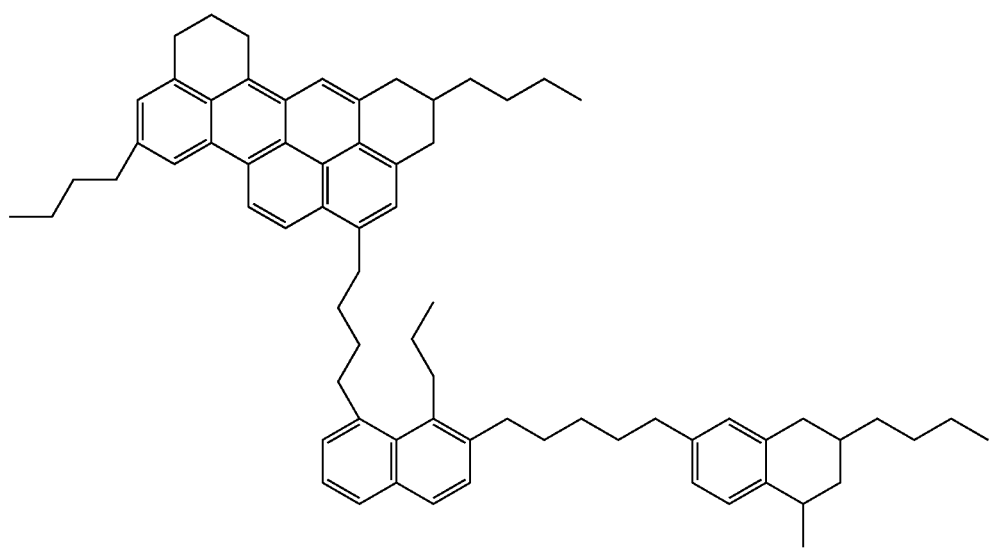

(A)

-continued

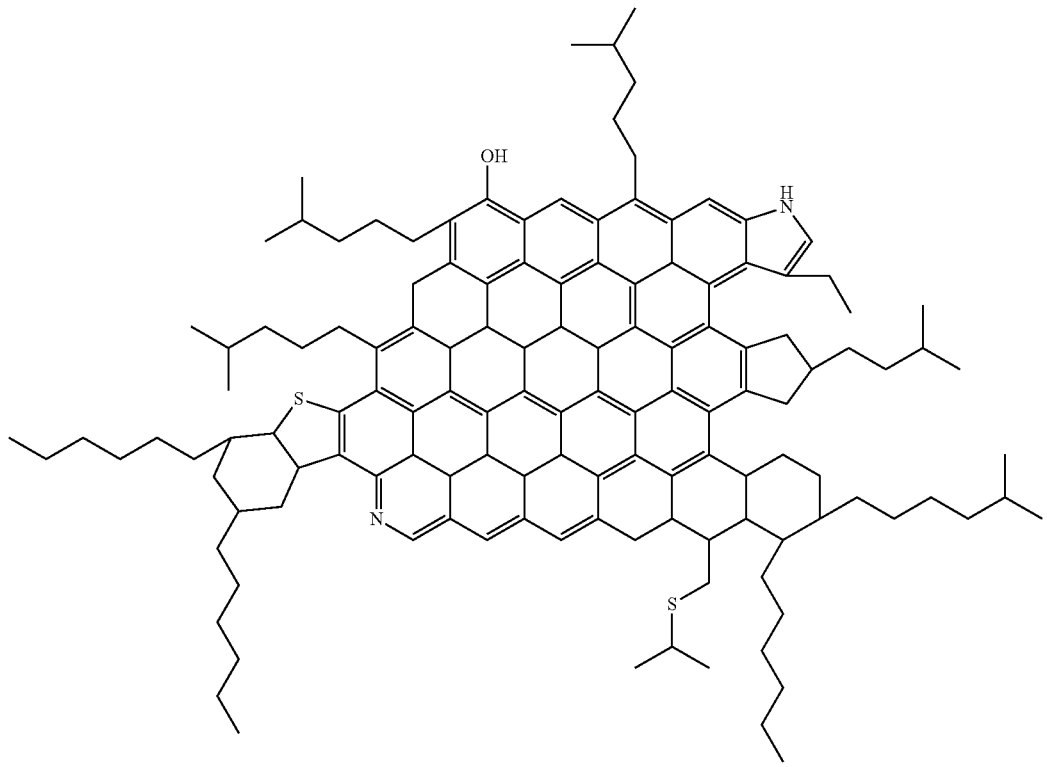

(B)

X-ray photoelectron spectroscopy may be used to determine the functional groups in the aromatic core. Oxygen is known to be present in asphaltenes in carbonyl, hydroxy and phenolic groups, including ketones and carboxylic acids and C—C linkages. All of these may be detected by X-ray photoelectron spectroscopy. In addition to identifying such functional groups, X-ray photoelectron spectroscopy may be used to identify nitrogen and sulfur in asphaltene. Sulfur is known to exist in asphaltenes as aliphatic sulfur, thiophenic and sulfoxide groups. Nitrogen is known to exist in aromatic groups such as pyrrolic, pyridinic and as tertiary amines. X-ray photoelectron spectroscopy may be used to determine the presence of nitrogen in pyrrole and pyridine rings as well as the presence of sulfur as thiophene and sulfones. X-ray photoelectron spectroscopy may also be used to determine the molar ratios of pyridine, pyrrole, sulfoxide and thiophene in the extracts.

Chemical bonds and functional groups in the aromatic core may be determined by the use of Fourier Transform Infra-Red Spectroscopy (FTIR). For instance, sulfoxide (S═O) and carbonyl (C═O), groups in the aromatic core may be detected using FTIR.

The aromatic nature of the core and the type of functional groups present in the asphaltene may further be determined by NMR. Typically, such content is determined by subjecting a portion of the asphaltene sample to solid state nuclear magnetic resonance $^1$H and $^{13}$C (NMR). The asphaltene sample is typically spun at its magic angle with respect to the direction of the magnetic field.

Based on the elemental analysis, FTIR, Raman spectroscopy, NMR and XPS, several possible structures can be derived for the aromatic core of the asphaltene.

In the second step of the process, geometry optimization calculations are performed on all structures by iteratively solving Hartree-Fock approximation to the Schrodinger Wave Equation. The electronic structure may be described using a 6-31G* basis set. This basis set can effectively describe C, H, O, S and N in the asphaltene. In the event heavier elements (transition metals) are present a bigger basis set may be required to describe the outer-shell electrons. Since the asphaltene is highly stable, those geometry optimized structures having the lowest free energy content are then selected.

The third step of the procedure is drawn to the determination of the aliphatic groups and functional groups attached to the aromatic core. Functional groups, as well as chemical bonds, may be determined from FTIR. For instance, hydrocarbyl chemical bonds, such as —$CH_3$, —$CH_2$ and —CH characterizing the asphaltene may be identified from the absorption bands provided in a FTIR analysis. NMR may further be used to enable determination of the aliphatic content and side chain content of the asphaltene. The presence of —$CH_3$, —$CH_2$ and —CH linkages in the asphaltene may further be determined from the $^{13}$C (NMR), as well as by subjecting a portion of the asphaltene sample to Distortionless Enhancement by Polarization Transfer (DEPT).

The addition of the side chains must be consistent with the population of different aliphatic groups (e.g. isopropyl, methylene and methine carbons) calculated from experiments.

The molecular weight distribution (MWD) of the asphaltene sample may further then be determined. The MWD is determined typically by subjecting a portion of the asphaltene sample to Laser Desorption/Ionization Molecular Weight Determination.

After determination of the molecular weight of the asphaltene sample, alternative molecular structures of particulates of the asphaltene sample may be determined from the collected data. Determination of one structure for the asphaltene is difficult due to aggregation of asphaltene molecules.

In the third step, geometry optimization calculations are performed on the possible configurations using Hartree-Fock theory and 6-31G* basis set. Partial charges on the atoms may then be calculated. In a preferred embodiment, in-vaccuo molecular dynamics simulations are performed on these structures. Conformations corresponding to the minimum, maximum and median value of the radius of gyration of the molecule during these simulations are selected. Single point energy calculations are performed on each conformation of the structures and the structures are subject to quantum chemistry modeling. The structure that has the lowest sum energy of conformational energy and isomerization energy is selected as the most probable structure.

In the next step, an appropriate catalyst system is developed for the molecular structure having the lowest energy. Development of the catalyst system is based on the bonds of the elucidated structure of the asphaltene. After the catalyst system is determined, fluid containing the asphaltenes is subjected to cracking in the presence of the catalyst system. The catalyst system breaks the functional groups within the asphaltene molecules. This results in reduction of asphaltene content in the fluid and an increase in saturates and aromatics content. The end result is a significant reduction in viscosity of the fluid.

The developed catalyst system is capable of breaking specific bonds of the core of the asphaltene since it is based on an elucidated structure of the asphaltene. For instance, a suitable catalyst would be one that breaks the C—S, C—C bond other functional group in asphaltene and hence reduces the viscosity of oil containing the asphaltenes.

In an embodiment, the catalyst system breaks the chemical bonds of at least one of the core structures of asphaltene. As stated, introduction of the catalyst can further decrease the activation energy and hence the reaction temperature. The viscosity of crude oil recovered from the reservoir is less than the viscosity of crude oil recovered from the reservoir which did not follow the methodology recited herein for catalyst selection.

The catalyst system is capable of breaking bonds identified in the asphaltene such that the asphaltene macromolecules are broken into smaller molecules. This results in the reduction of asphaltene content and an increase in saturates and aromatics contents in the crude oil. Consequent to this process is a significant reduction in viscosity of heavy oil. The reduction in viscosity of the fluid containing the asphaltenes is determined, along optionally with analysis of the composition of the asphaltene. If the reduction in viscosity is acceptable, the catalyst system is then introduced downhole to break up the asphaltene. Should the asphaltene sample be ineffectively broken down, then a second catalyst system may be developed selected based on the bonds of the core structure. The process may further be repeated until an ideal catalyst system is developed which effectively breaks the bonds of the asphaltene or a reduction in viscosity is observed in the fluid containing the asphaltene.

Potential catalysts within a catalyst inventory are those which attack various functional groups such as carbonyl, acid and alcohol group present in the asphaltene molecules. Thus, based on the functional groups and the structure of the aromatic core of the elucidated structure of the asphaltene, components of the catalyst system are selected.

For instance, where the asphaltene structure is determined to have hydrocarbon chains, basic catalysts may be selected. Such catalysts specifically attack hydrocarbon chains and break carbon-carbon bonds. Solid base catalysts include those supported with MgO and having transition metal functionalities.

The catalyst inventory from which the components of a catalyst system may be developed may further include solid acids, such as zeolites. Zeolites attack peripheral hydrocarbon chains attached to the asphaltene molecule. Certain zeolites however, suffer from drawbacks such as durability, stability and coking. The zeolite catalyst may thus be modified to make it stable under conditions such as in hot water with active metals Ni, Mo and/or Co. Such modified zeolites may be used to reduce the viscosity of heavy oil via mild cracking at relatively low temperatures.

Further catalysts in a catalyst inventory which may be used in the development of a catalyst system are bimetallic and monometallic oxide/sulfides of transition metals. These include nanostructure catalysts which can more readily adsorb asphaltenes than micro size catalysts and reduce the viscosity of crude oil significantly.

Further, specific metal catalysts which target the alicyclic group in the aromatic core of the asphaltene molecule have been identified. For example, the Ni-W catalysts supported on the USY zeolite may be use to break tetralin by ring opening as follows:

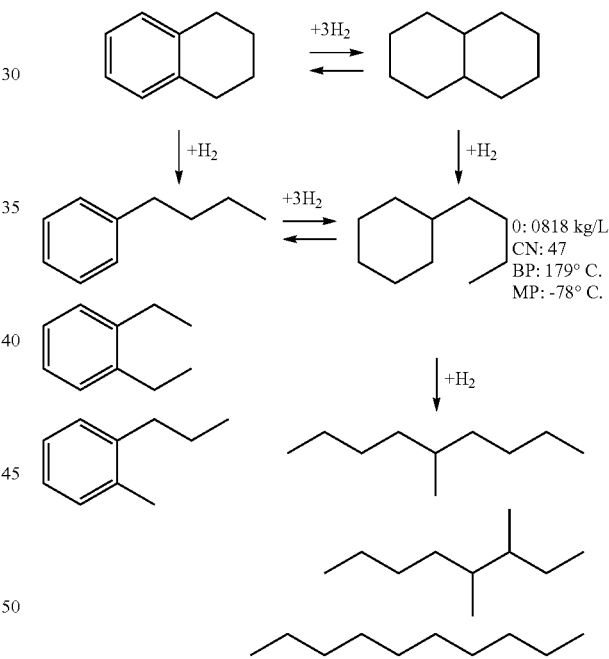

Further, precious metal catalysts such as Pt—Ir/TiO$_2$ and Pt—Ir/Al$_2$O$_3$ are useful for tetralin ring opening reactions. Monometallic Pt and Rh as well as bimetallic Pt—Rh catalysts are known to be more active and exhibit bifunctional behavior, with alumina facilitating acidic function and ring opening reaction.

Cracking of phenyl heptane with metal modified Y-zeolite catalyst has been shown to produce smaller hydrocarbon molecules. Cracking in a long alkyl side chain results in a carbenium ion that easily isomerizes and causes self-alkylation of the aromatic ring. Two cracking mechanisms may occur: a monomolecular mechanism involving proton attack either on the benzene ring or on a sigma C—C bond in the alkyl chain (protolytic cracking) and a bimolecular mechanism involving carbenium ions, chain transfer via hydride transfer and β-scission, as illustrated by the following:

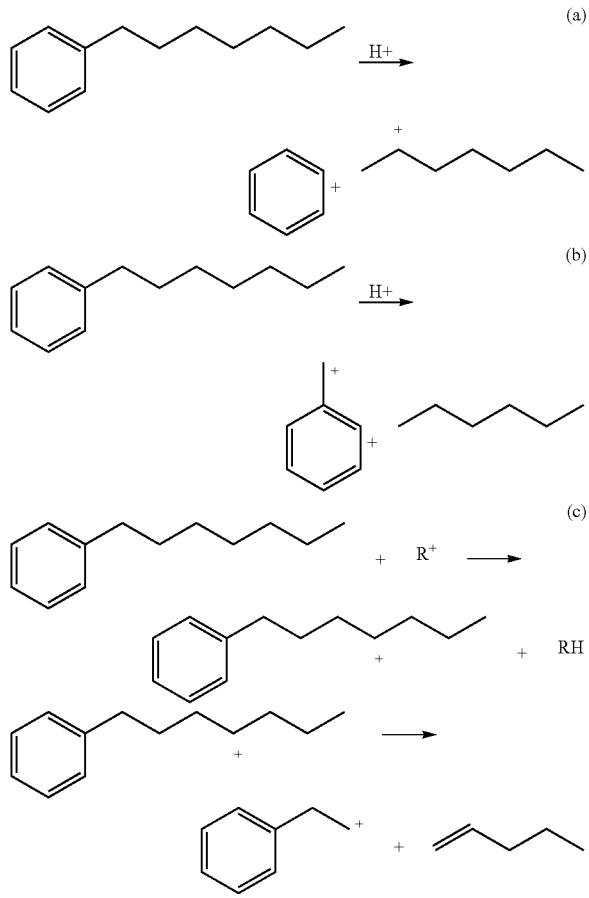

Further, where the asphaltene macromolecules have C—S and C—N bonds, the catalyst system may include a transition metal catalyst. Such components are especially effective in the breaking of thiophene and pyrrole linkages. For instance, Ni and Mo are effective for sulfur removal from the thiophene and benzothiophene moieties. They also break the C—N bond in the pyrrole linkage in the asphaltene molecule.

Further, a catalyst of Co(Ni)—Mo(W)S/Al$_2$O$_3$ may be used for hydrodesulfurization reactions. Generally, sulfided NiMo/Al$_2$O$_3$ catalysts are more active for hydrodesulfurization (HDS) and hydrodenitrogenation (HDN) than sulfide CoMo/Al$_2$O$_3$ catalysts. The transition metals Mo and W combined with V, Nb, Cr, Mn, and Co, are more active catalysts for sulfur removal.

Further, acceptable catalyst systems include those set forth in U.S. patent application Ser. No. 15/173,476, filed on Jun. 3, 2016, herein incorporated by reference. Such catalyst components include first row transition metals such as Cr, Fe, Mn, Ni, Co with the support CeO$_2$, MgO, zeolite, SiO$_2$, etc. which are effective in the breaking of C—C, C—S, C=O, —OH and acid groups in the aromatic core of the asphaltene molecule.

Figure 2:
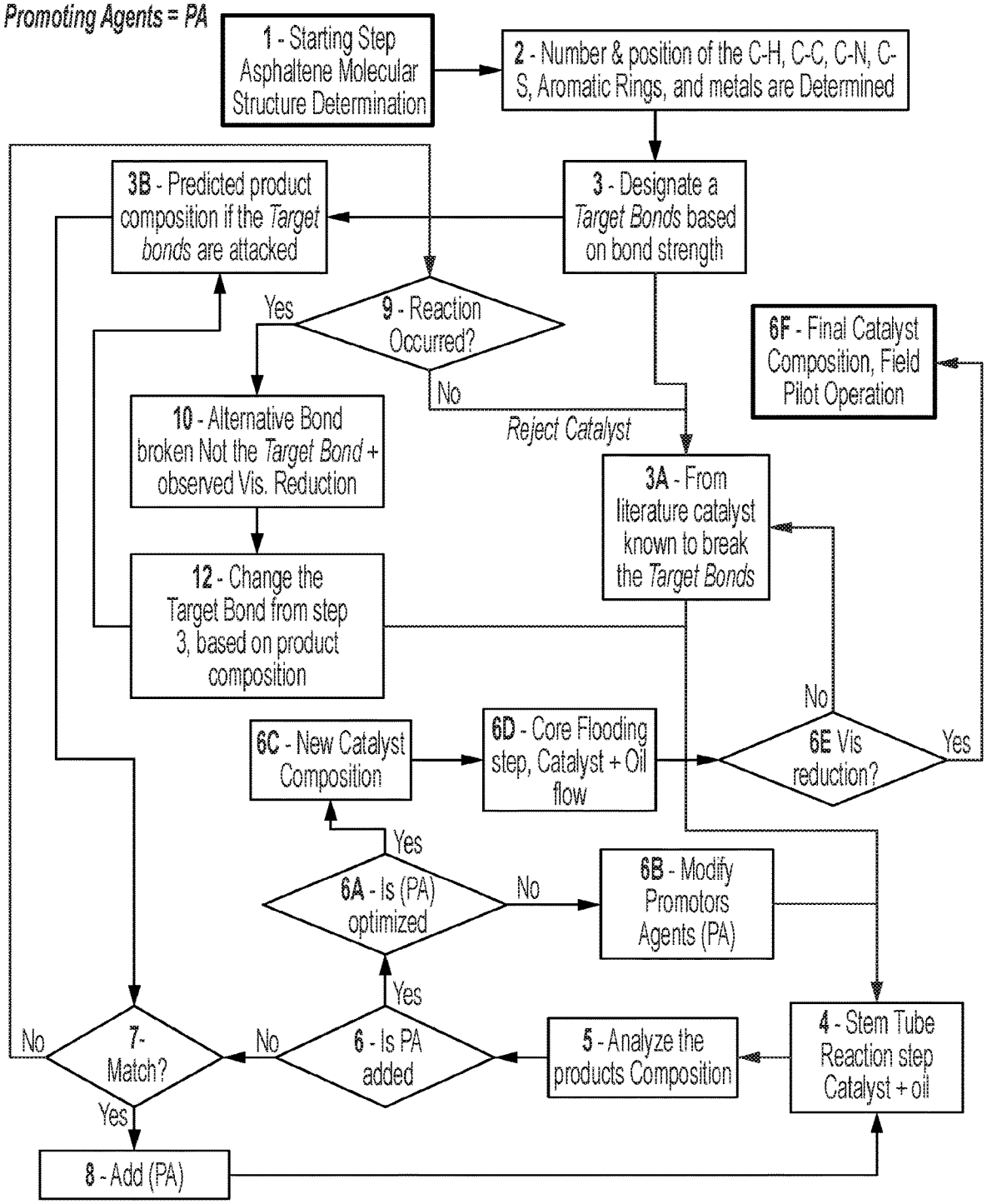
FIG. 2 represents an exemplary flow diagram for the process of structure elucidation of asphaltene in a crude oil sample followed by catalyst selection for crude oil viscosity reduction.

FIG. 2 depicts a method for developing a catalyst system in basically three series of steps. The first series of steps may be referred to as target bond determination. The number and position of the carbon-hydrogen, carbon-carbon, carbon-nitrogen and carbon-sulfur bonds as well as the aromatic rings and metals are known from the determined molecular structure of the asphaltene (steps 1 and 2). The weakest bonds are chosen as the potential bonds for catalytic reaction within the molecular structure (step 3). Relative strengths of the various bonds may be obtained from literature; for example, a carbon-sulfur bond is relatively weaker than a carbon-carbon bond. Therefore, the carbon-sulfur bond(s) could be identified as a potential target bond. The existence of certain aliphatic chains or aromatic components in the asphaltene can also be predicted based on the target bond. This could serve as a confirmation that the target bond was attacked during a catalytic reaction.

In the second series of steps, catalytic activity is assessed based on the Target bond(s). One or more catalysts from the literature (the catalyst inventory) may be selected for the target bond(s). For instance, catalysts used in refineries for hydrocarbon cracking may be selected initially. For example, it is known that higher molecular weight hydrocarbon molecules are preferentially cracked over an acidic metal-containing hydrocracking catalyst. Table 1 shows examples of catalyst which contain acidic functionality support and hydrogenating components and having cracking and hydrogenation functionalities.

TABLE 1

| Support (Cracking components) | Active components (Hydrogenation components) |
|---|---|
| Al$_2$O$_3$, MgO | Co/Mo |
| SiO$_2$—Al$_2$O$_3$, CeO$_2$ | Ni/Mo |
| TiO$_2$—Al$_2$O$_3$ | Pt/Pd |
| Zeolites | Ni/W |

It could be anticipated that a suitable catalyst with a combination of hydrogenation and acidic functionalities would crack asphaltenes at temperatures ranging from 200° C. to 250° C. The product yield (catalyst efficiency) may be determined by initial feedstock composition, catalyst selectivity, and process conditions. The product composition is analyzed after completion of the reaction (steps 4 & 5). Since the reaction is shown as being conducted in tube reactors without the benefit of a promoting agent (PA), the product composition from the analysis may be compared to the predicted composition from step 3B (based on the target bond choice from step 3), step 7. If the catalyst has attacked a target bond an overall match between the predicted composition (step 3B) and the actual resulting composition (step 5) is noted along with a substantial reduction in viscosity as noted in Step 10. However, in light of the diversity of molecular structures in heavy oil, an exact compositional match will never likely be obtained (step 7). Due to adsorption properties on the catalyst surface or existence of a functional group on the aromatic core the catalyst could attack a bond (step 10) other than the one predicted in step 3. In such case, the composition of the product will not match with the predicted composition in step 3B. However, if viscosity has been lowered (step 10), the catalyst and product compositions could then be used to assess product toxicity (step 11) and assist in the selection of a new target bond (Step 12) and a new prediction of product composition (step 3B) with the catalyst being tested. (Steps 9, 10, 11, 12 & 3B in order). To validate catalytic reaction with the new target bond from step 12 the catalyst is retuned to step 4 for another cycle of testing but with new choice of target bonds (step 12) and predicted product composition steps 12 & 3B. If there are no correlations between the product and predicted compositions or if the product contains free heavy metal (toxic) or sulfur compound (detrimental to refinery process) then the catalyst is rejected and a new catalyst is chosen for another cycle of reactions. (Steps 9, 3A & 11, 3A).

In the third series of steps, a promoting agent is chosen to improve catalyst activity. The promoting agent, with the catalyst, forms the catalyst system. This series of steps may include combining metals and metal oxides as promoting agents with catalysts, increasing specific surface area through size reduction (nanoparticle synthesis), ligand formation of metals with electron donating ligands and selection of a suitable support material for the catalyst particles.

The promoting agent is added to the catalytic reaction to enhance the product composition (break more variety of target bonds) or increase the yield (increase the amount of the products generated). An iterative process is typically required in order to optimize the promoting agent based on the highest yield or concentration and diversity of products (molecular structures) that achieve the lowest viscosity (steps 8, 4, 5, 6, 6A, 6C) compared to the oil viscosity at step 4A.

To verify the activity of the catalyst (obtained in step 6C) at reservoir conditions, the process may be repeated in a flow reactor using a core flooding apparatus, step 6D. If the reaction occurs as predicted, then a reduction in viscosity should be observed as compared with the original sample viscosity, step 4A. In this case the final catalyst composition is ready field pilot operation, steps 6E & 6F.

More details of the process are set forth in the following Example drawn to determination of the structure of an asphaltene extracted from a Canadian crude oil.

Example 1. Extraction of Canadian asphaltene. Canadian asphaltenes were extracted from crude oil as follows. Crude oil (10 g) was added to a 1000 mL round bottom flask equipped with a condenser. Heptane (1 g crude oil:40 g heptane) was then added and the resulting mixture was refluxed for 1 hr. The mixture was cooled and the solid asphaltene was filtered in vacuo to separate the asphaltene from maltenes (liquid phase) and the solvent heptane. The resulting black solid was dried to get the asphaltene.

Elemental Analysis. Elemental Analysis identified the ratio of carbon, hydrogen, nitrogen, oxygen and sulfur (in mol percent) and the amount of nickel, vanadium and iron in ppm. The elements present in the asphaltene extract were analyzed as follows: carbon, hydrogen, and nitrogen with a PerkinElmer 2400 Series II CHNS/O Analyzer using combustion, oxygen by a Thermo Finnigan FlashEA™ Elemental Analyzer, sulfur by a LECO SC-432DR and the metals by Inductively Coupled Plasma Atomic Emission Spectrometry. The results are set forth in Table II.

TABLE II

| Sample | C % | H % | N % | O % | S % | V ppm | Ni ppm | Fe ppm |
|---|---|---|---|---|---|---|---|---|
| Mean Average | 78.83 | 7.57 | 1.275 | 1.75 | 7.9 | 1029.5 | 380.5 | 763.5 |

The molar weight ratio of hydrogen:carbon was calculated to be 1:14. Based on the H:C ratio derived from elemental analysis, the type of asphaltene was determined to be an island type. Had the H:C<1.28, it would have been a rosary type.

Figure 3:
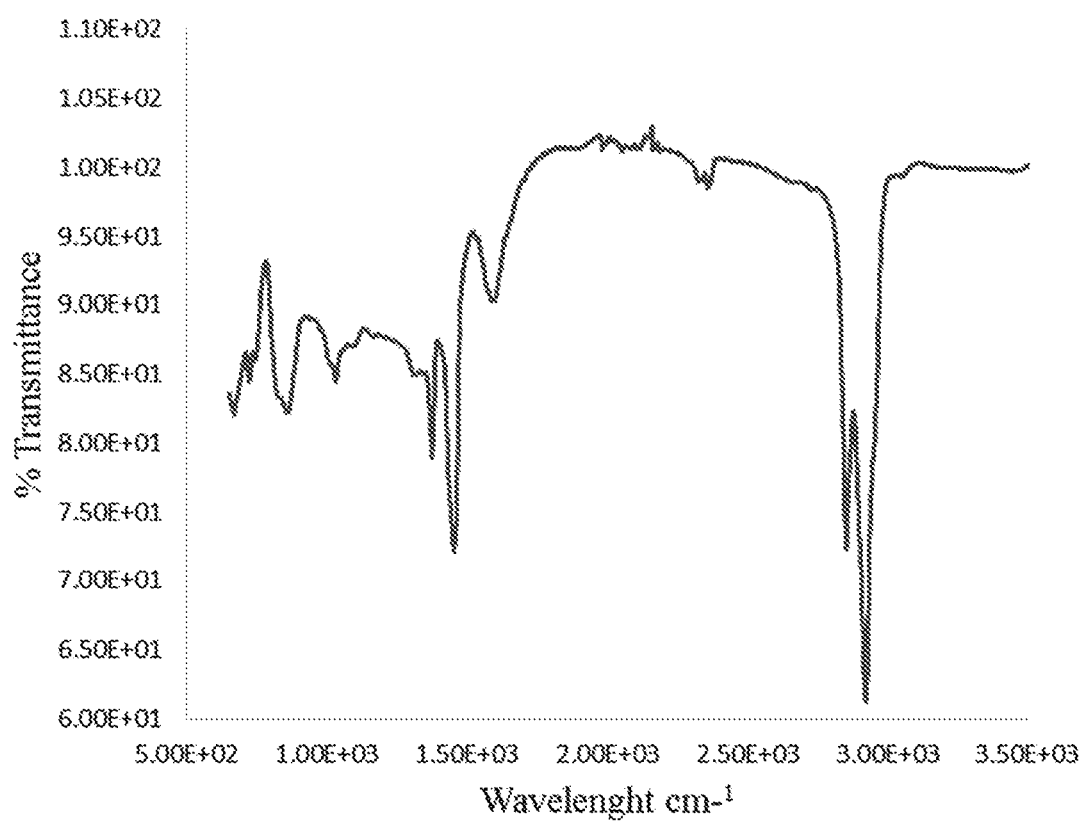
FIG. 3 is a spectra of a Fourier Transform Infrared Spectroscopy (FTIR) of a Canadian Oil asphaltene extract.

Fourier Transform Infra-red Spectroscopy (FTIR) was used to provide information on the functional groups present in the asphaltene. FTIR spectra were recorded in transmission mode using Nicolet FTIR benchtop and microscope system. Diamond was used as the sample holder for the process. From the absorption bands, the functional groups and chemical bonds in the sample were determined. The results, shown in FIG. 3 illustrate C=C, C—H and S=O functional groups.

Nuclear Magnetic Resonance Spectroscopy. The asphaltene extracts were subjected to different types of nuclear magnetic resonance (NMR) spectroscopy and provided information on the aromatic and aliphatic percentage, the type of side chains present and the structure of the asphaltene (to be either rosary or island).

Figure 4:
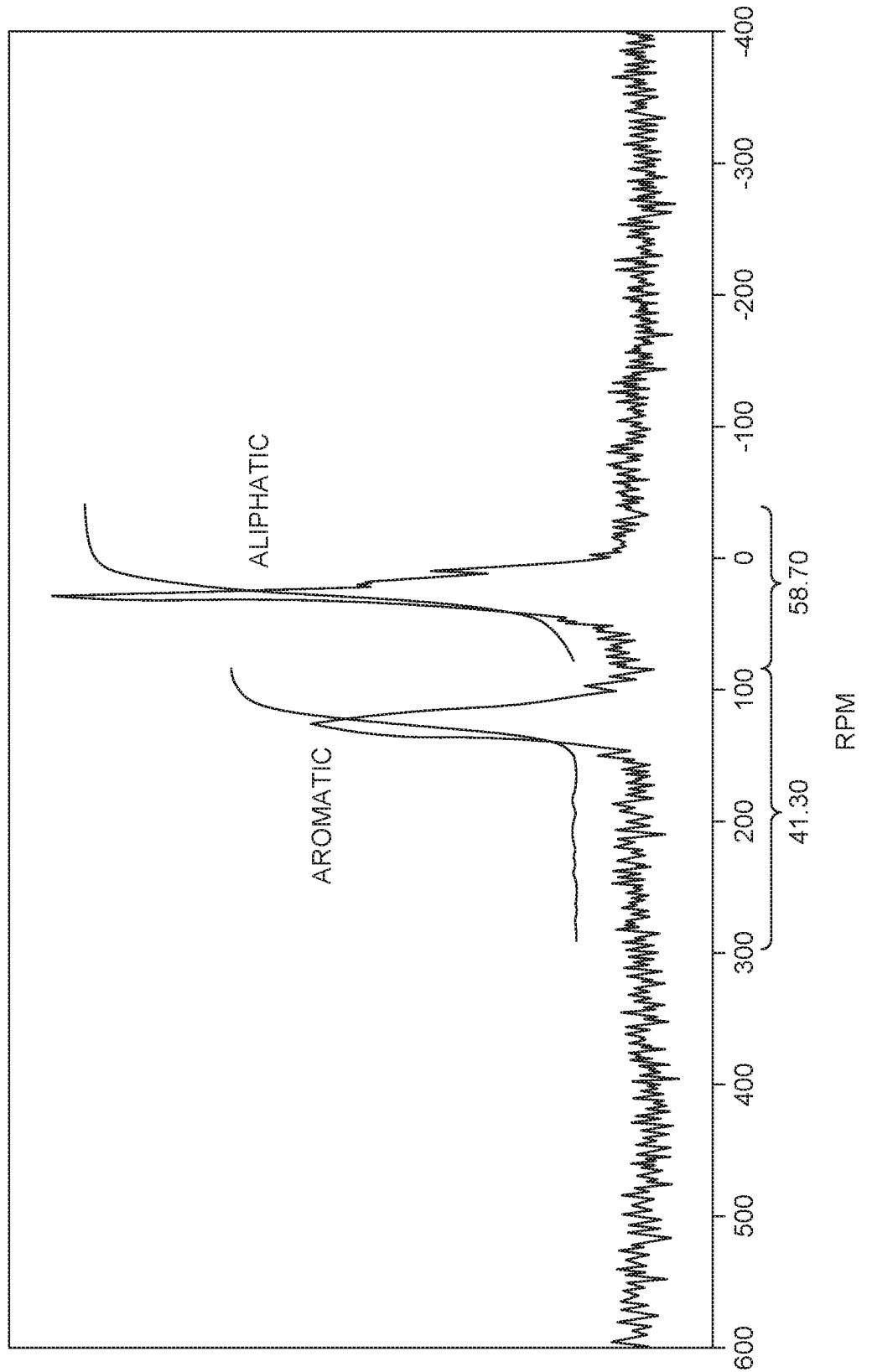
FIG. 4 is a solid-state $^{13}C$ NMR of a Canadian Oil asphaltene showing 41% aromaticity.

Solid-state $^{13}$C NMR spectra were obtained on a Bruker AVANCE-200 NMR spectrometer (50.3 MHz $^{13}$C, 200.1 MHz $^1$H). The asphaltene extract was packed in a 4-mm outer diameter rotor. Chemical shifts were reported relative to the carbonyl carbon of lysine at 176.46 ppm. The percentage of aromatic and aliphatic groups in the Canadian asphaltene was determined to be 41% and 59% respectively. Also, the $^{13}$C NMR showed us the presence of phenolic group in asphaltene (FIG. 4).

Figure 5:
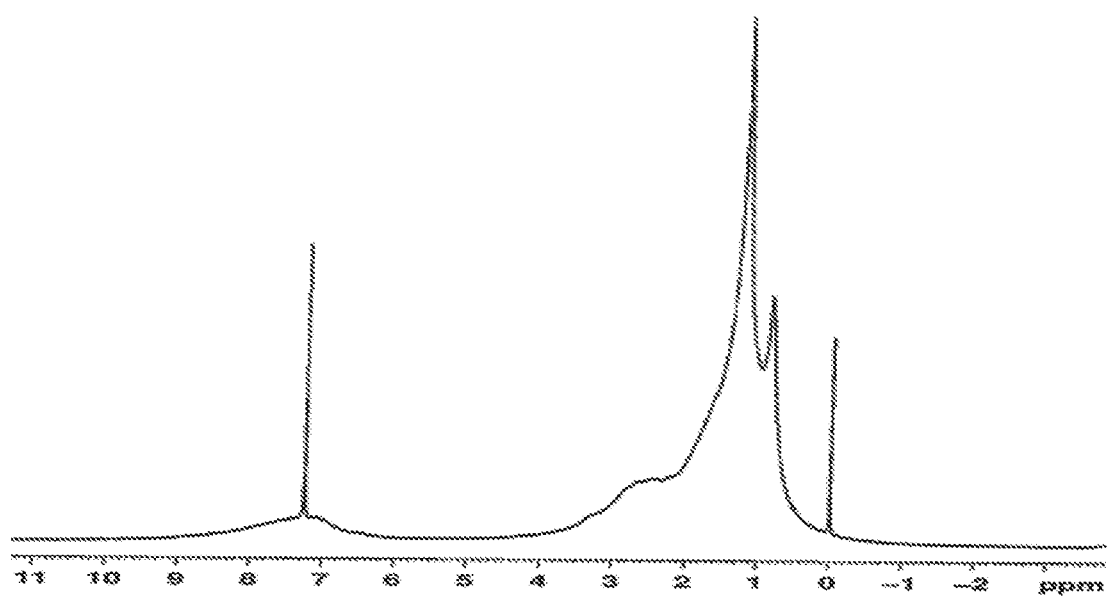
FIG. 5 is a solution state $^1H$ NMR of a Canadian Oil asphaltene.

Solution state spectra were acquired using standard pulse programs on a Bruker Advance III, 2-channel spectrometer with an 11.7 T magnet (125.7 MHz $^{13}$C, 500.1 MHz $^1$H) and a broadband ($^{15}$N—$^{31}$P) observe/$^1$H decoupling probe for 5 mm tubes with automated tuning and matching of both rf channels and a z-axis gradient coil. The asphaltene extracts were dissolved in CDCl$_3$ with 0.05% TMS. Solution $^1$H NMR, shown in FIG. 5, provided information on the side chains. The following observations could be concluded from solution $^1$H NMR:

CH$_2$ adjacent to CH$_3$ of propyl or longer alkyl chains,
CH$_3$ carbons of isopropyl groups terminating moderately long n-alkyl chains,
CH$_3$ branches in the interior of moderately long n-alkyl chains; and aromatic CH$_3$ groups.

Figure 6:
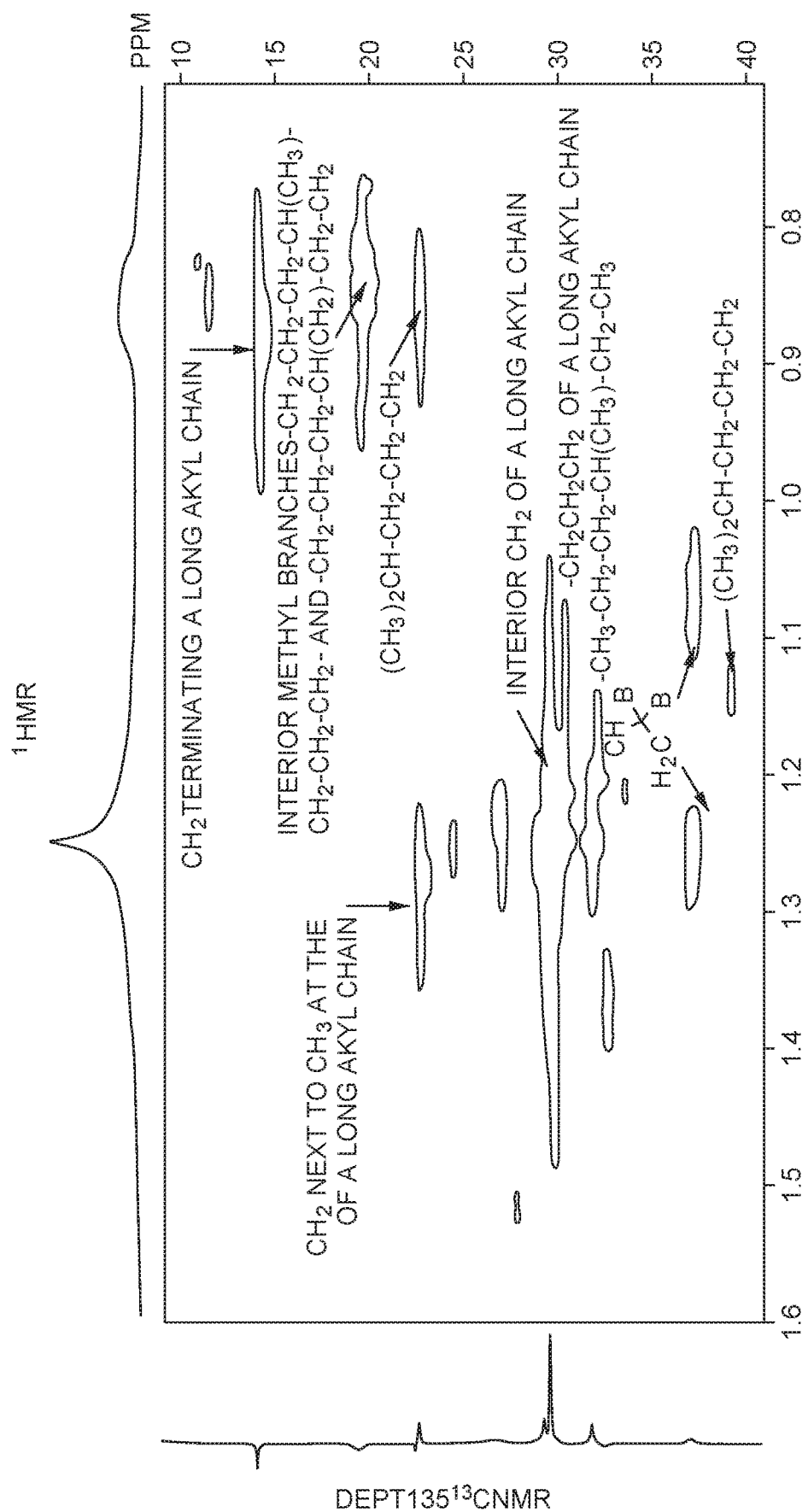
FIG. 6 is a two-dimensional NMR HSQC (DEPT135 $^{13}C$ and $^1H$) NMR of a Canadian Oil asphaltene.

$^{13}$C Distortionless Enhancement by Polarization Transfer (DEPT-135) experiments were optimized for $^1J_{CH}$=145 Hz, while $^1$H-$^{13}$C HSQC experiments were optimized for $^1J_{CH}$=125 Hz because of the particular interest in the aliphatic region. The DEPT-135 $^{13}$C spectra, shown in FIG. 6, shows the aliphatic structures of the asphaltene as having —CH$_2$ next to —CH$_3$ at the end of an alkyl chain, methine of isopropyl group, —CH$_3$ of ethyl branch, methyl branch on alkyl chain, —CH$_3$ from isopropyl CH$_3$ and diastereotopic —CH$_2$ next to a chiral center (methyl branch).

Figure 7:
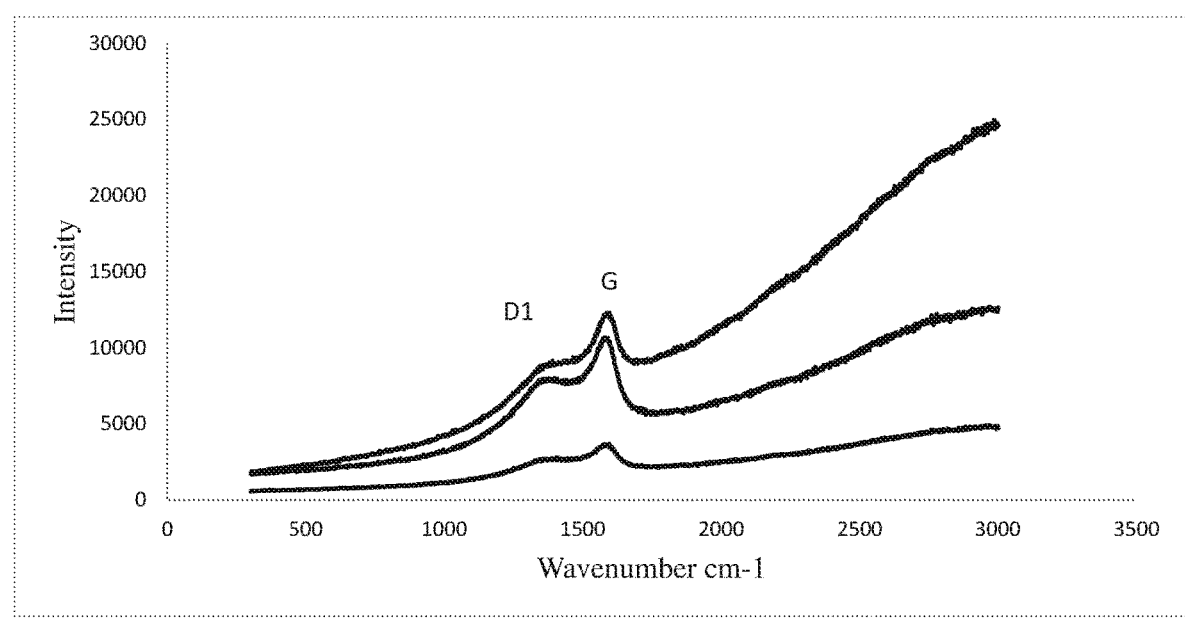
FIG. 7 is a Raman spectra of a Canadian Oil asphaltene showing homogeneity within the sample.
Figure 8:
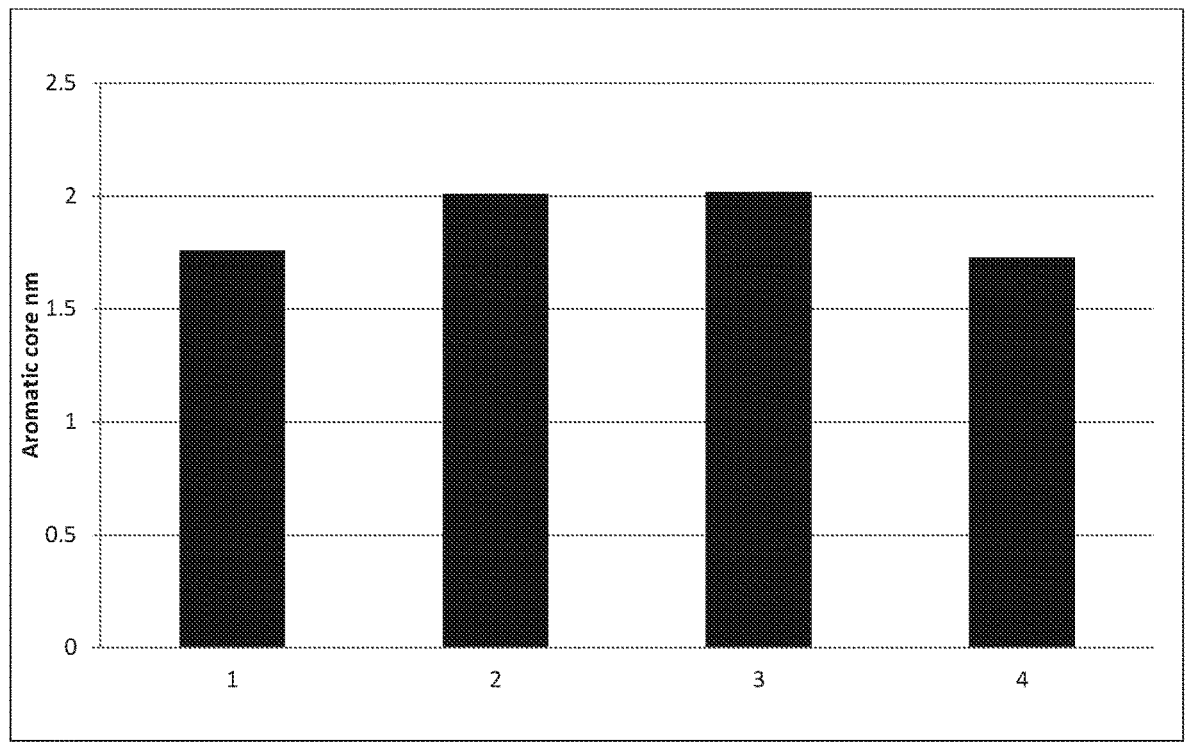
FIG. 8 shows the aromatic core size of a Canadian Oil asphaltene from different locations.

Raman Spectroscopy. Raman spectra were collected using Reinshaw 1000 micro-Raman system equipped with a 514-nm laser source. The Raman spectra were collected for each sample from three different locations to examine sample homogeneity. The results are illustrated in FIG. 7. To make proper peak assignments of the Raman spectroscopic data Peakfit software was used to process the data. The Gaussian function was used to fit the best number of peaks. The size of the core (number of benzene rings fused together) was calculated based on the Tuinstra and Koenig equation $$L(\text{nm}) = 4.4 \times \frac{I_G}{I_{D1}}; L = \text{Diameter of aromatic core size in nm}$$

$$I_G = \text{Intensity of } G \text{ band and } I_{D1} = \text{Intensity of } D1$$

and was found to be 1.73-2.02 nm indicating the core is made up of 6-7 benzene rings, FIG. 8.

Figure 9:
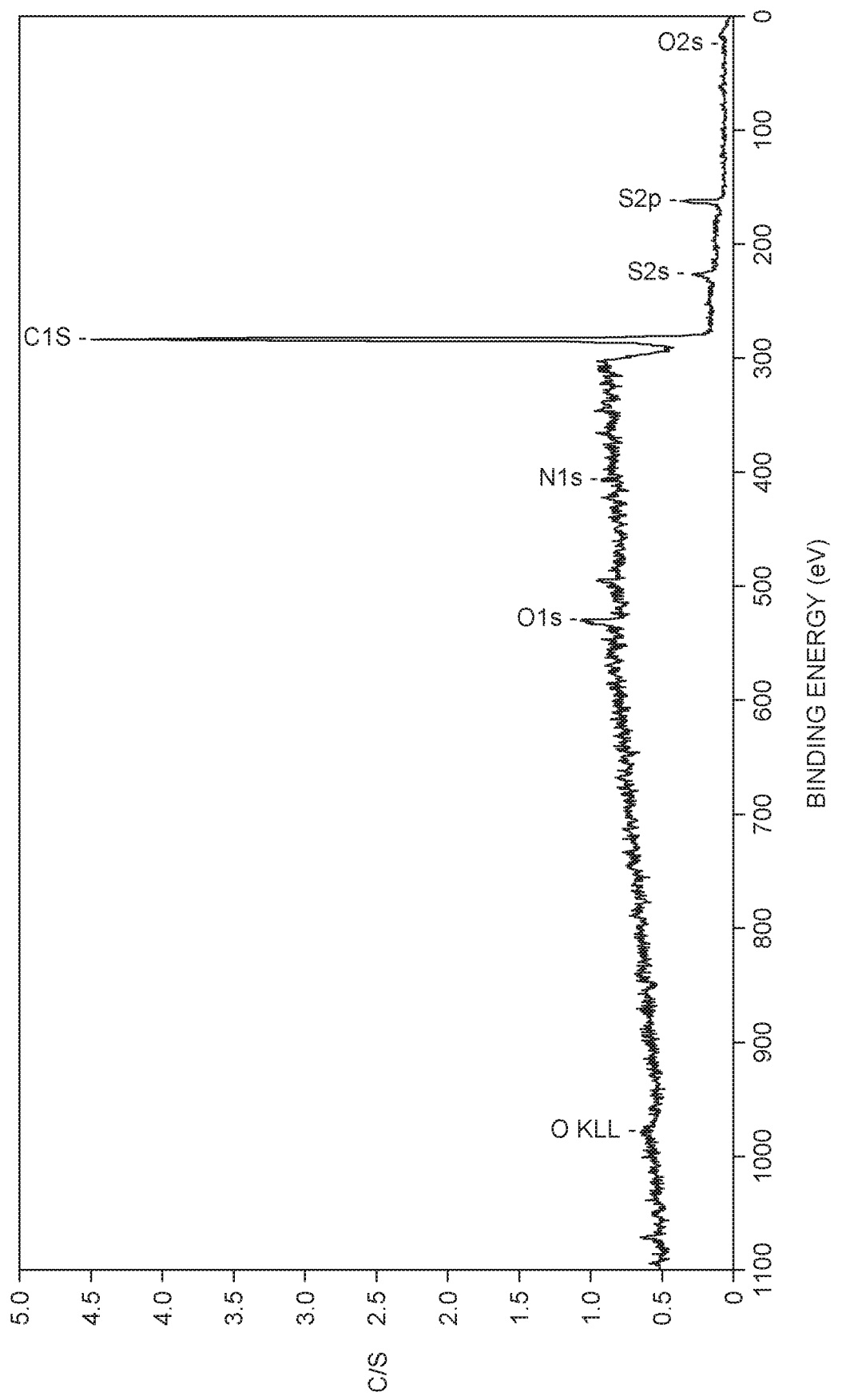
FIG. 9 is a survey XPS spectra for a Canadian Oil asphaltene.
Figure 10A:
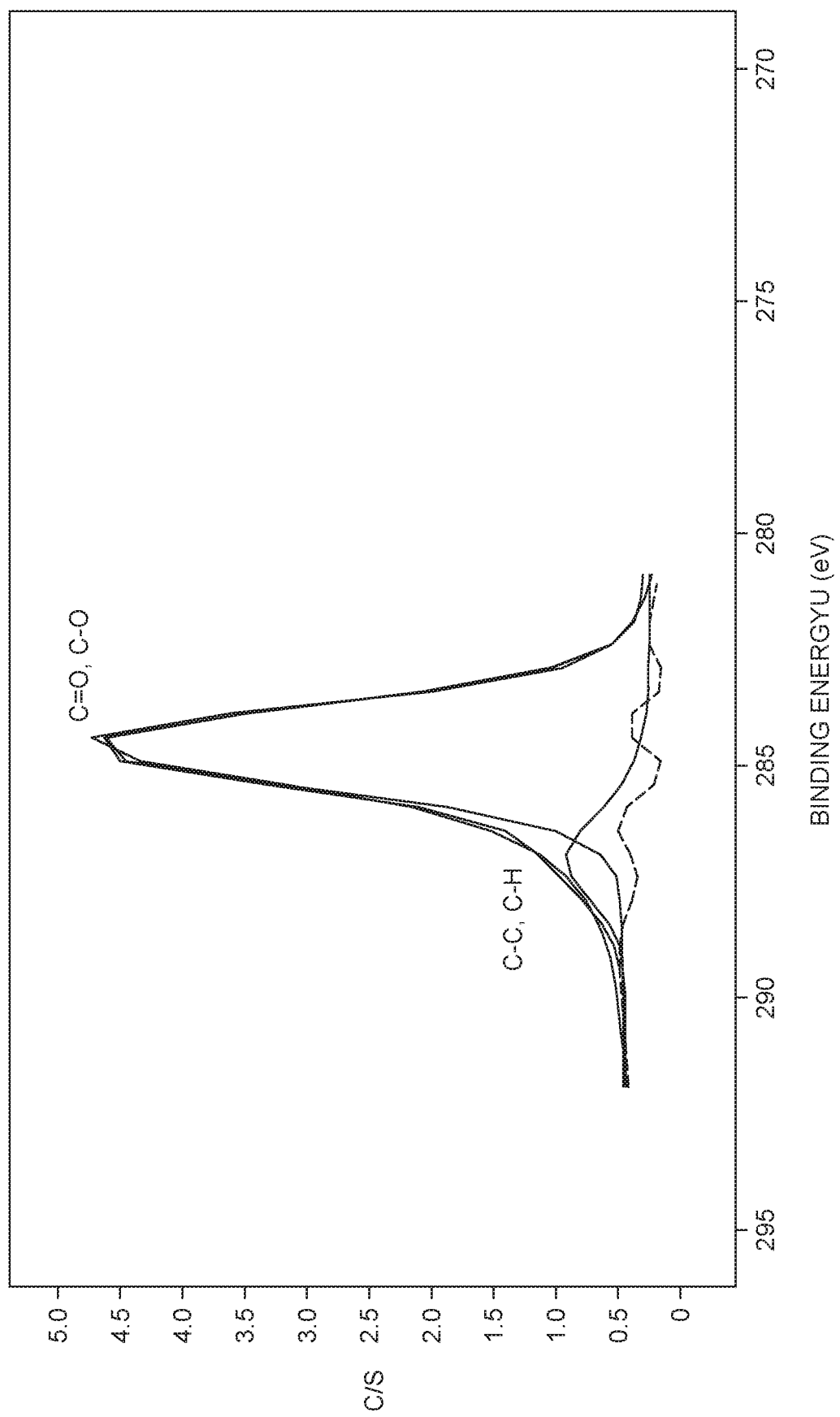
FIGS. 10(a), (b), (c) and (d) are deconvulated XPS spectras for carbon, sulfur, nitrogen and oxygen, respectively, of a Canadian Oil asphaltene.
Figure 10B:
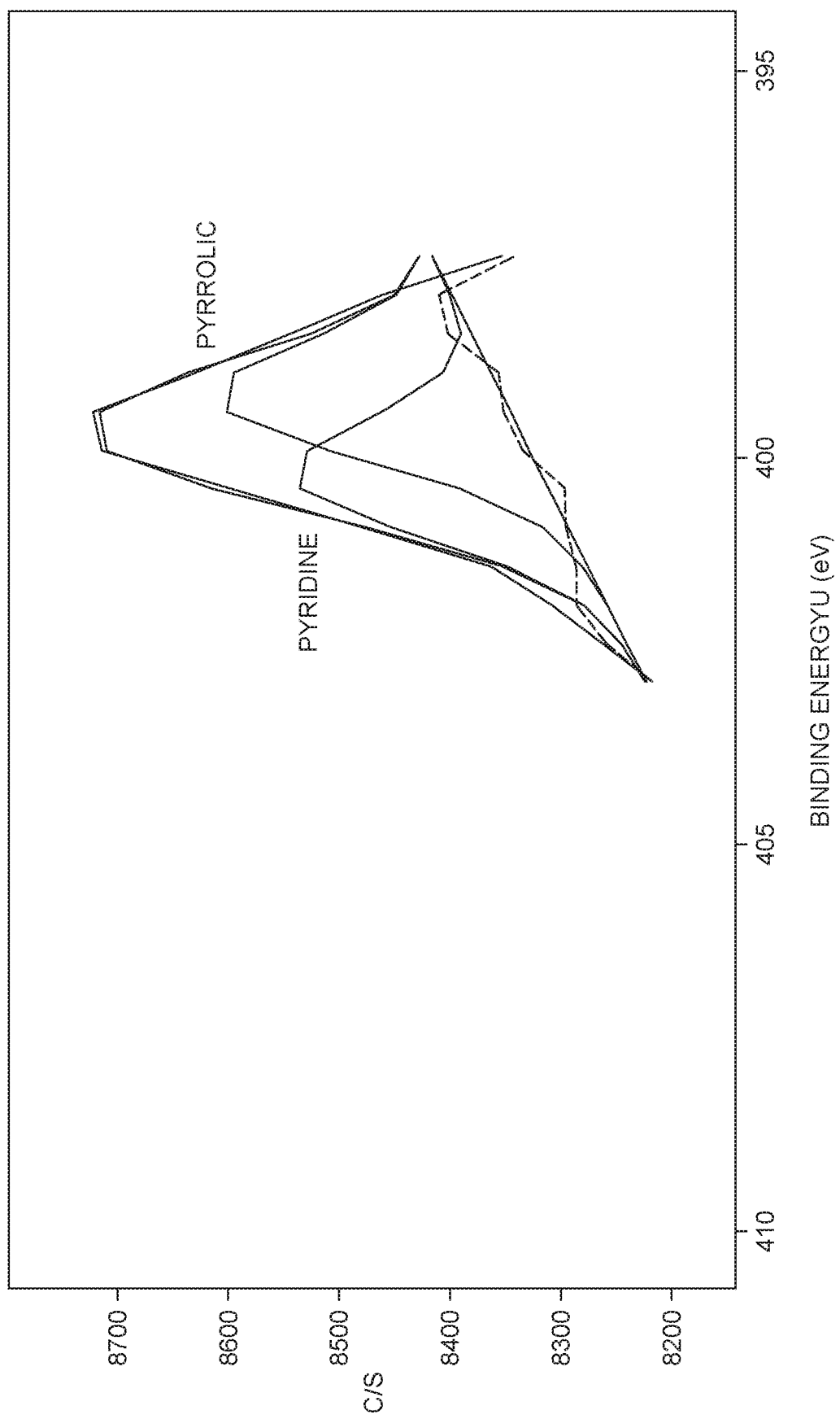
Figure 10C:
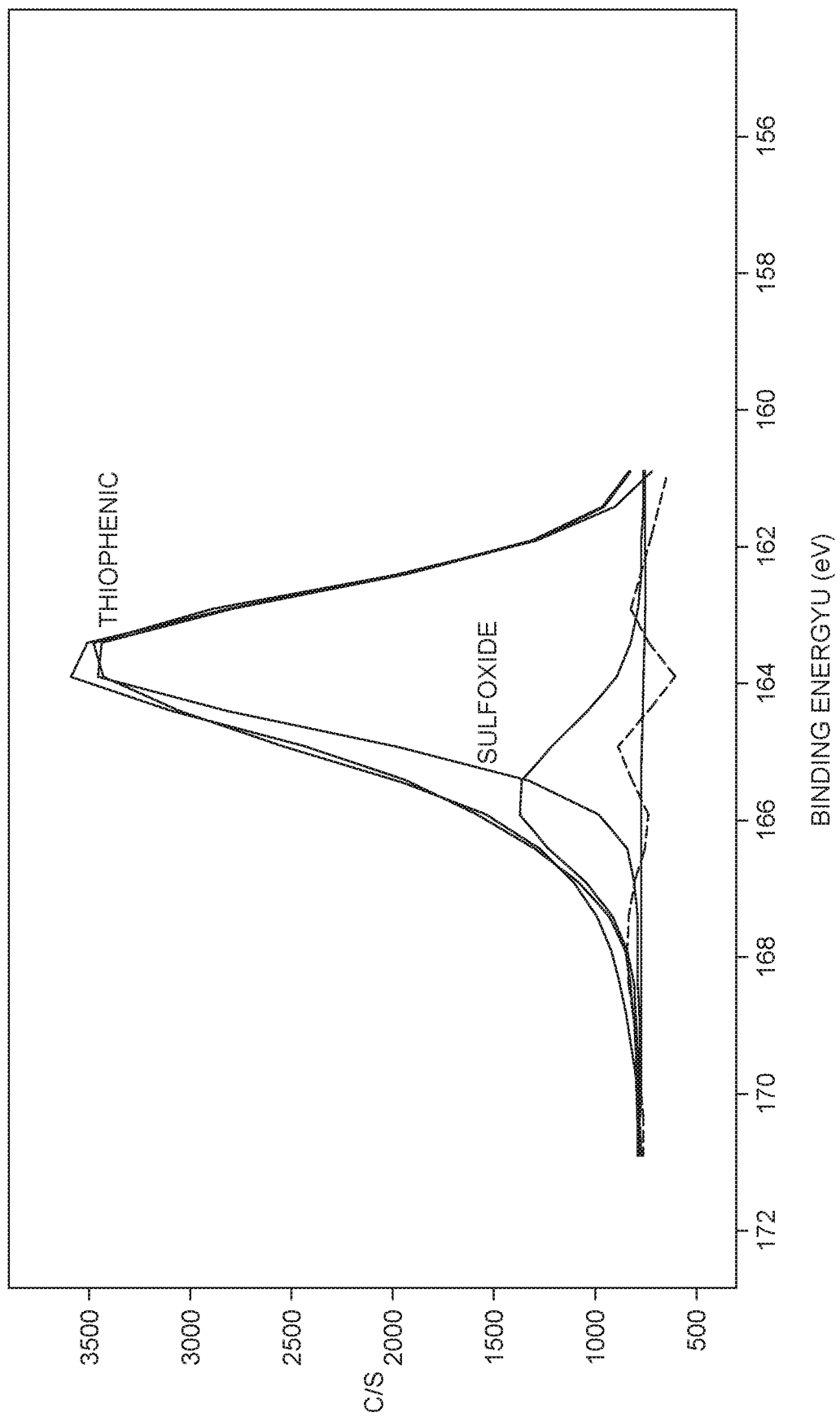
Figure 10D:
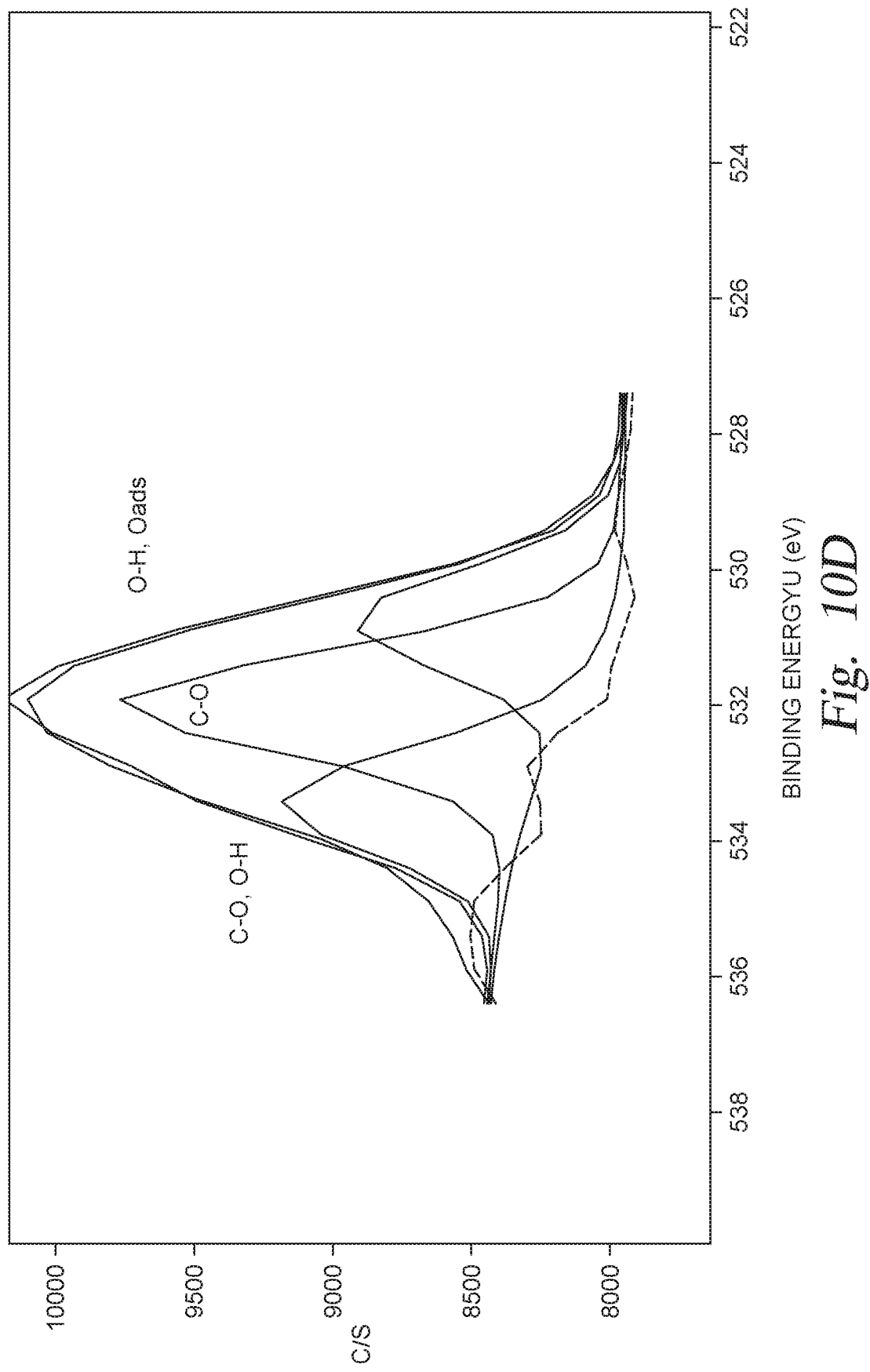

X-ray Photoelectron Spectroscopy. The forms in which carbon, hydrogen, nitrogen and sulfur were present in the asphaltene extracts were determined by x-ray photoelectron spectroscopy (XPS). A Physical Electronics (PHI QUANTERA) XPS/ESCA system was used to acquire the XPS data. The base pressure of the system was 5×10$^{-9}$ Torr. A monochromatic Al X-ray source at 100 W was used with pass energy of 26 eV and a 45-degree takeoff angle. The results are illustrated in FIG. 9. The spectra showed the presence of heteroatoms oxygen, nitrogen and sulfur and carbon—the major component of asphaltene. Individual peaks of each atom were deconvoluted to give the information on the type of linkage each individual heteroatoms present in the molecule, shown in FIGS. 10(a), (b), (c) and (d). Deconvoluting each of the individual element peaks enhances prediction of the type of bonds or functional groups present in the extract. Table III shows the percentage, binding energy and structural information for atoms present in the Canadian oil asphaltene by XPS.

TABLE III

| Element | Binding energy (eV) | Percentage | Separation (eV) * | Structural information |
|---|---|---|---|---|
| C | 284.59 | 86.48 | 0 | C—C, C—H |
|   | 287.01 | 10.52 | 2.42 | C═O, C—O |
| S | 163.66 | 80.17 | 0 | Thiophenic |
|   | 165.66 | 19.83 | 2.0 | Sulfoxide |
| N | 399.26 | 53.26 | 0 | Pyridine |
|   | 400.28 | 46.74 | 1.01 | Pyrrolic |
| O | 530.72 | 26.07 | 0 | O—H, Oads |
|   | 531.94 | 48.59 | 1.22 | C═O |
|   | 533.39 | 25.33 | 2.67 | C—O, O—H |

* Separation between the deconvoluted lowest binding energy band and other bands for each set of elements Synthetic methods. The Canadian oil asphaltene was then subjected to analysis by various synthetic methods.

Figure 11:
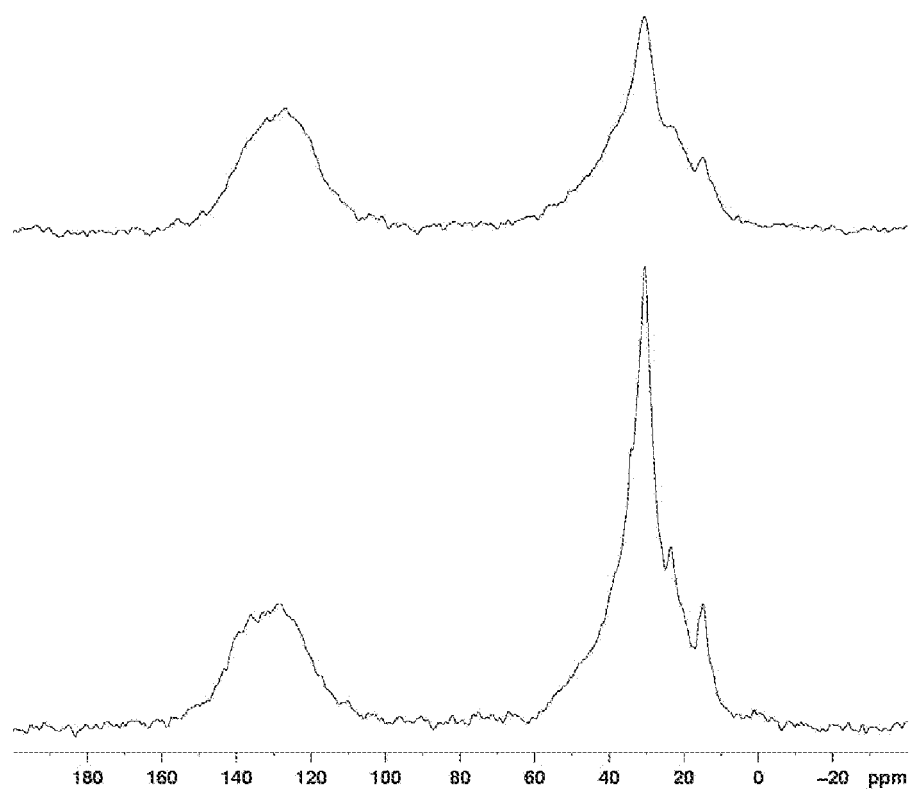
FIG. 11 is a Comparison of $^{13}C$ NMR of a Canadian Oil asphaltene (a) with dodecylated asphaltene (b)

In the first method, reductive alkylation on that asphaltene was conducted with iodo-dodecane via Birch reduction. This lead to the attachment of a C12 alkyl side chain on the asphaltene. The study by NMR of the dodecylated asphaltene and the starting asphaltene confirmed the side chain length in Canadian oil asphaltene to be less than C12. There is greater height of the CH2 linkage in the dodecylated asphaltene compared to starting asphaltene as confirmed by $^{13}$C NMR and illustrated in FIG. 11.

The synthetic reactivity of the asphaltene extract was further illustrated with 2,3-dichloro-5,6-dicyano-1,4-benzoquinone (DDQ) using the uniqueness of DDQ to change a cyclic system to an aromatic system. The asphaltene extract (100 mg) and DDQ (2 equivalents) were added to a three-neck flask under inert gas condition containing 15 ml of solvent toluene. This mixture was heated overnight under inert atmosphere. The solvent toluene was removed by rotary evaporator and then the solid material obtained was purified by adding toluene and filtering the impurities. Purification of the black product was further repeated by adding toluene until the filtrate had no color. Aromaticity of the asphaltene extract sample was shown to increase after the reaction. An increase in the aromaticity of the dehydrogenated system of asphaltene by DDQ, giving a direct indication that the Canadian oil asphaltene had a cycloalkane type of system.

Incorporating the data along with the constraints of maintaining symmetry and maximizing the number aromatic 6 π electron i.e. benzene type moieties (Clar' s sextet rule) forms the basis of designing the core. The core in the asphaltene extract was determined using the analytical data set forth in Table IV:

TABLE IV

| Raman | 7 aromatic rings |
| FTIR | C═C, C═O, C—H, S═O |
| XPS | Pyridine, Pyrrole, Thiophene, Sulfoxide |
| NMR | 41% aromatic; 59% phenolic |
| H:C (elemental analysis) | 1.14 |
| Reaction (DDQ) | Presence of cycloalkane rings |

The following four core structures were then designed based on the analytical data which comply with the Clar's sextet rule.

(i) Cores without S═O and C═O groups in the core

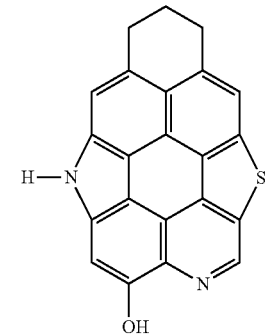

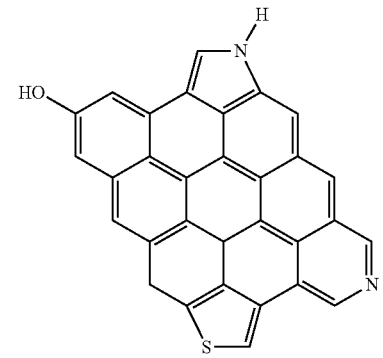

(ii) Cores with S═O and C═O groups in the core

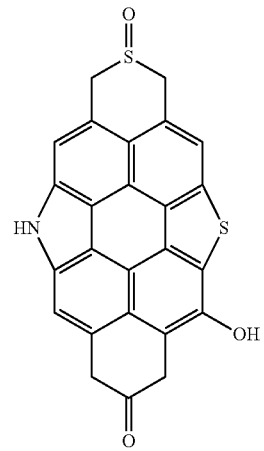

-continued
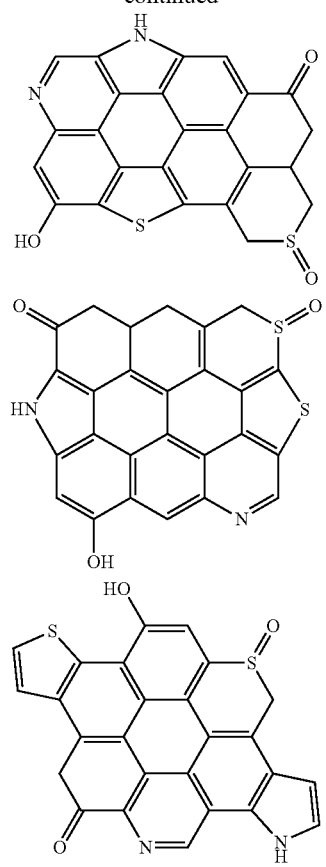
(iii) Cores with only S=O group in the core
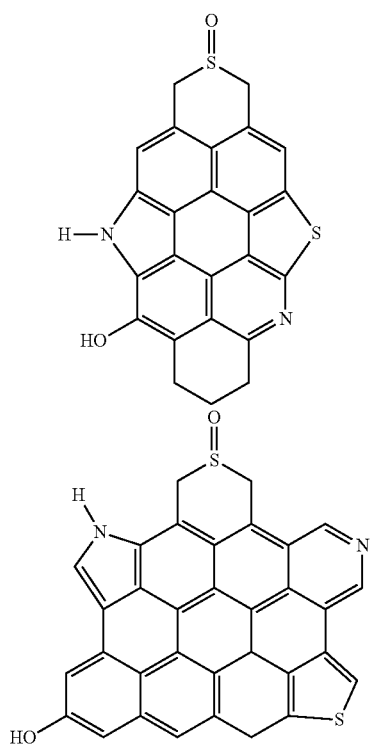
-continued
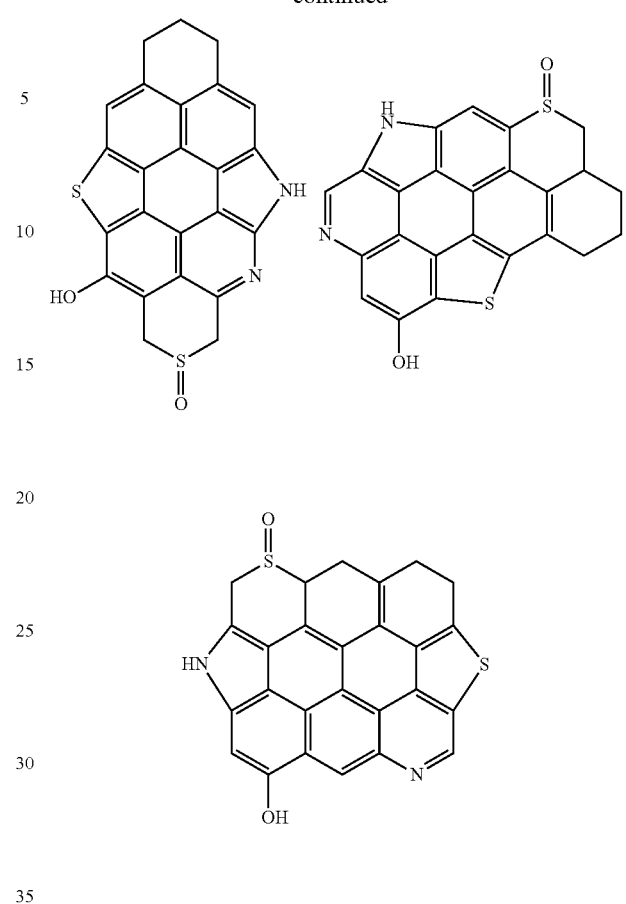
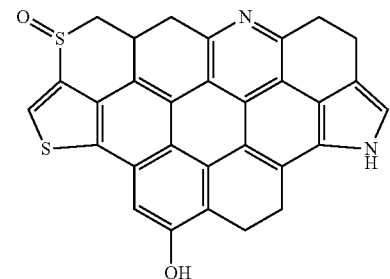
(iv) Cores with only C=O group in the core
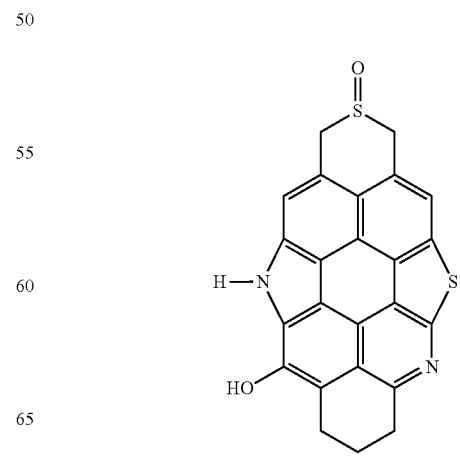

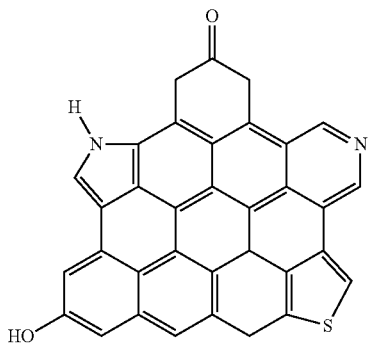

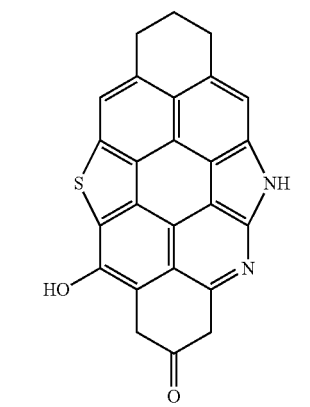

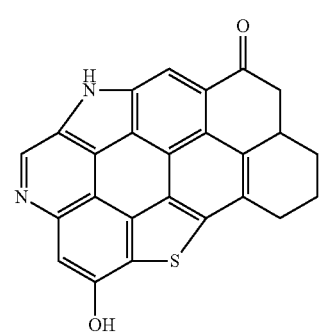

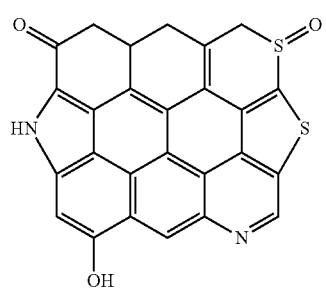 [SMILES: O=C1CC2CC3=c4c5c(sc6cnc7cc8c(O)cc9[nH]c1c1c2c4c(c7c65)c8c91)S(=O)C3]

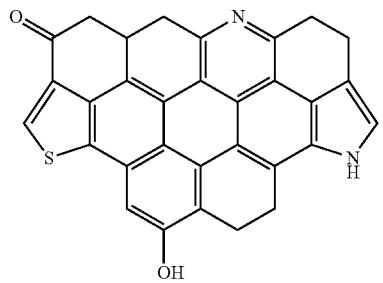

To determine the most probable structure, the electronic energies of each of the core structures were performed using geometry optimization calculations using the Hartree-Fock level of theory and 6-31G* basis set.

Figure 12:
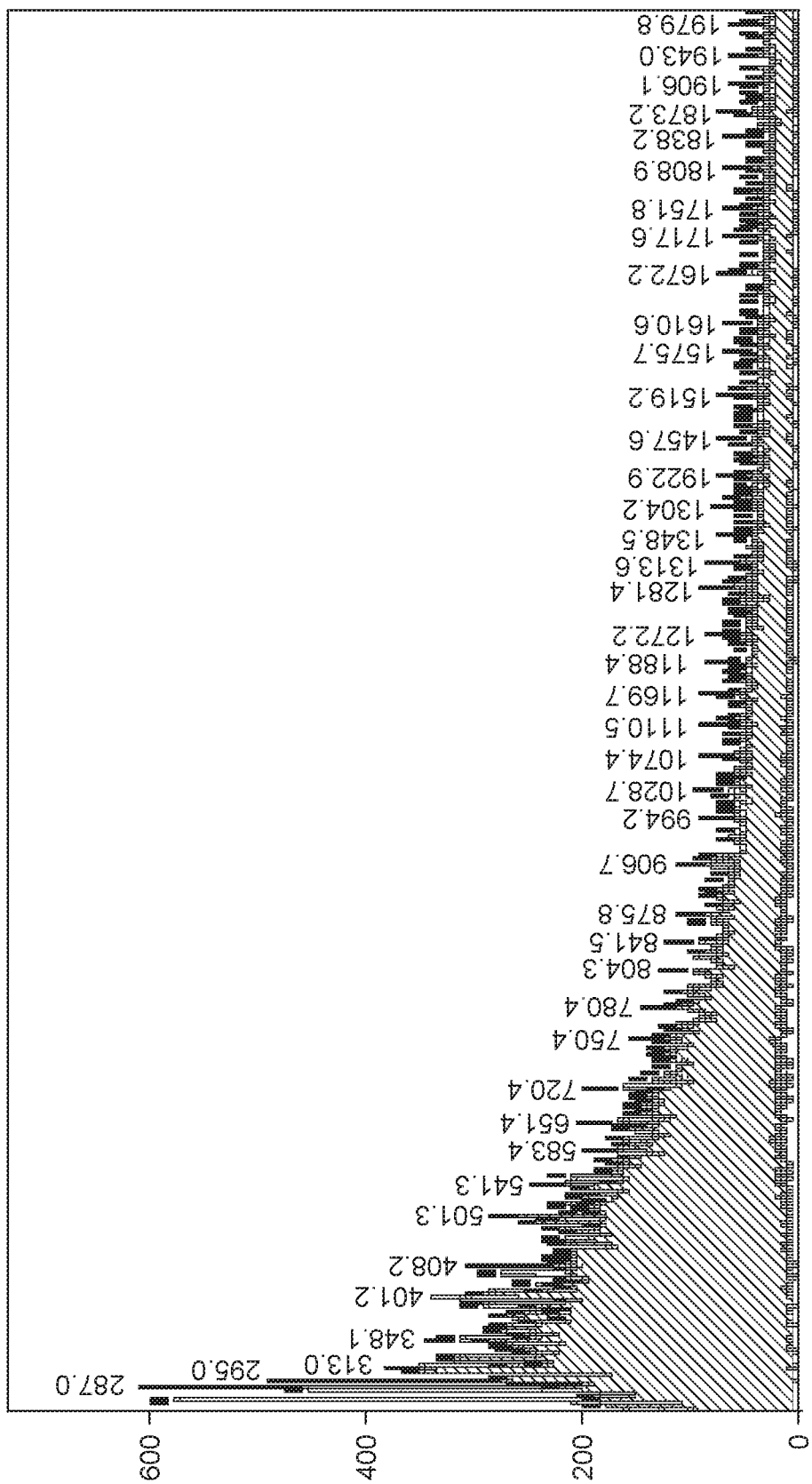
FIG. 12 is a Laser Desorption/ionization spectra of a Canadian Oil asphaltene.

Laser Desorption/Ionization. The molecular weight distribution of the asphaltene extract was determined using Laser Desorption/Ionization (LDI). This provided information on the molecular weight of the core and the estimated molecular weight of the asphaltene extract. A sample was prepared by dissolving ~5 mg of the asphaltene extract in 2 mL of tetrahydrofuran (THF). For LDI analysis the stock solution was either directly spotted on the LDI plate for analysis. LDI analysis was carried out on the Bruker Auto-Flex MALDI Mass Spectrometer. A hump in the range of 200 to 800 was observed in the LDI spectra, shown in FIG. 12, the maxima observed being 320.7 Da, which corresponded to the molecular weight of the asphaltene core (without considering the fragile groups easily broken out during the process under normal operating conditions of the Spectrometer. The tail/end of the hump provided the molecular weight of the Canadian oil to be greater than 850-900 Da.

The lowest energy structure matching the LDI defragmentation pattern and molecular weight closest to the experimental data showed the most probable core structure for the Canadian oil asphaltene to have a molecular weight of 413 Da (on breaking the fragile group in the process of LDI will lead to a molecular weight distribution of 314-338 Da).

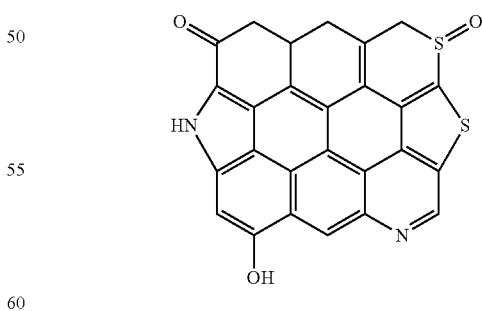

Based on LDI, NMR, elemental analysis, XPS and FTIR data, the side chains were added to the core. The resulting structure should match the molecular weight from LDI, aromaticity from NMR, H/C from elemental analysis and the functional groups from FTIR and XPS. The following possibilities were presented:

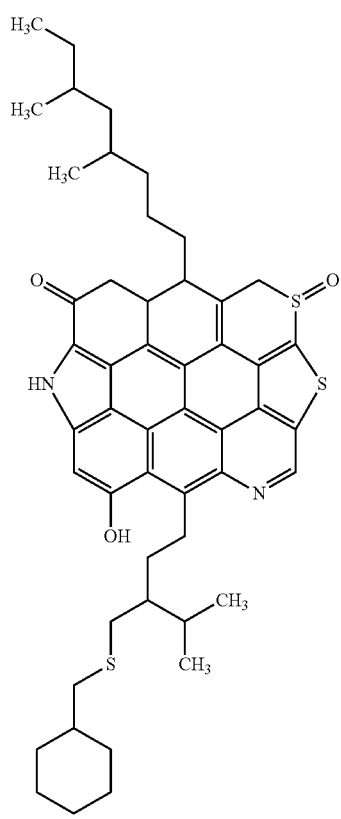
(1)
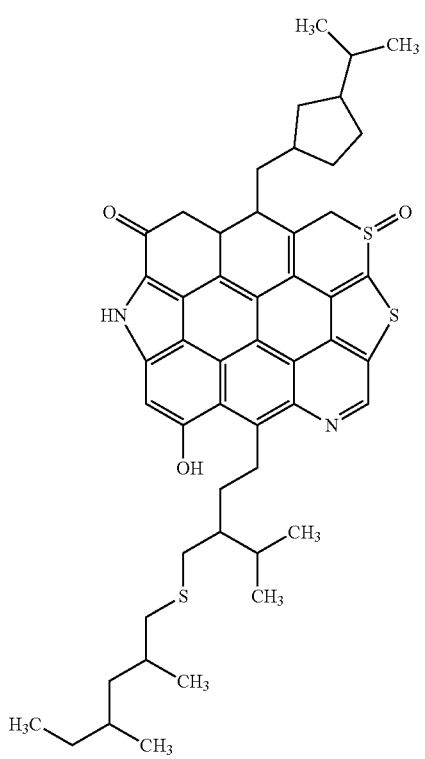
(3)
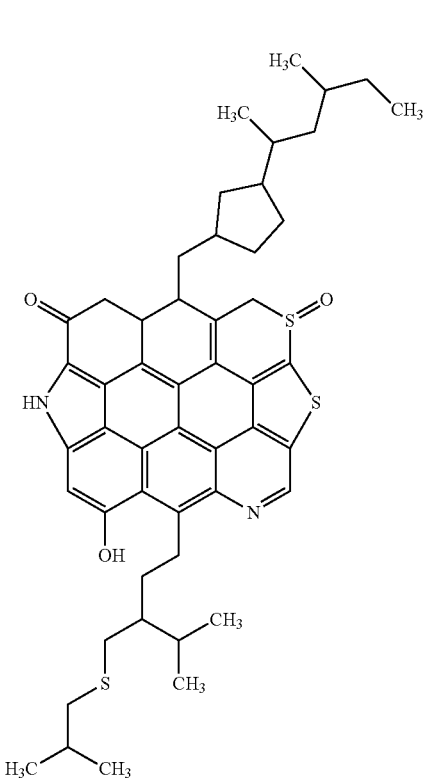
(4)

-continued

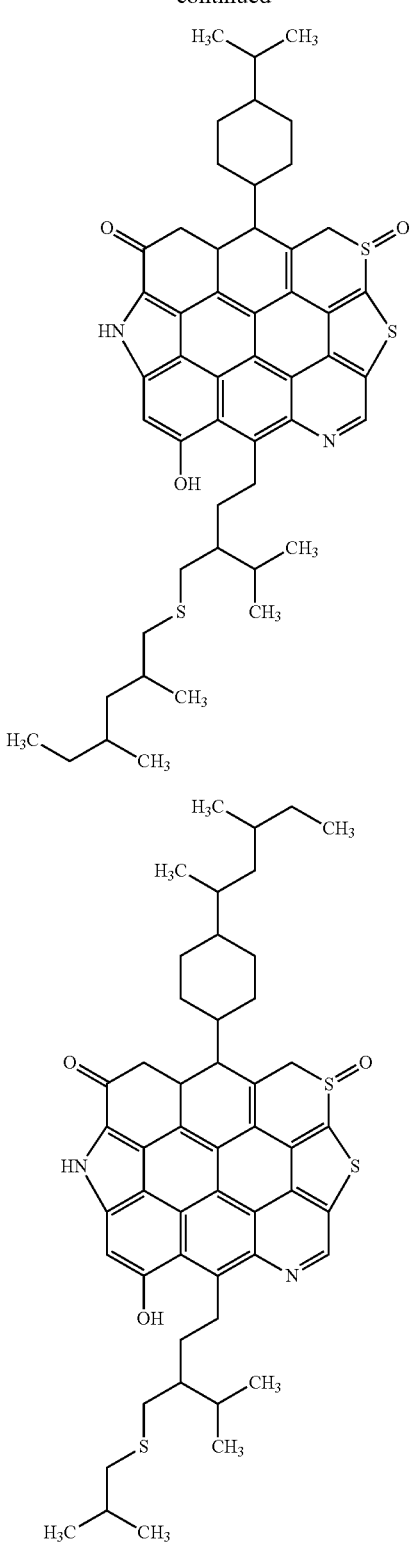

(5)

(6)

To determine the most probable structure, geometry optimization of each of these structures was performed using Hartree-Fock level of theory and 6-31G* basis set which can effectively describe C, H, O, S and N. Partial charges on the atoms were calculated on the geometry optimized structure using Restricted Electrostatic Potential (RESP) method.

Molecular dynamics simulations at 573 K in an isochoric-isothermal ensemble (NVT) in a cubic box of volume 15.625 nm³ were performed on each structure to review all possible conformations in the phase space. The radius of gyration of the molecule was calculated at every 10 steps of simulation using trajectories from the molecular dynamics simulations. The radius of gyration was used as an order parameter to determine the probability of a certain conformation. Three different conformations based on minimum, maximum and median value of the radius of gyration were sampled for each molecular structure:

1. minimum radius of gyration corresponding to the folded conformation;
2. maximum radius of gyration corresponding to the extended conformation; and
3. median radius of gyration corresponding to the most probable conformation.

Figure 13:
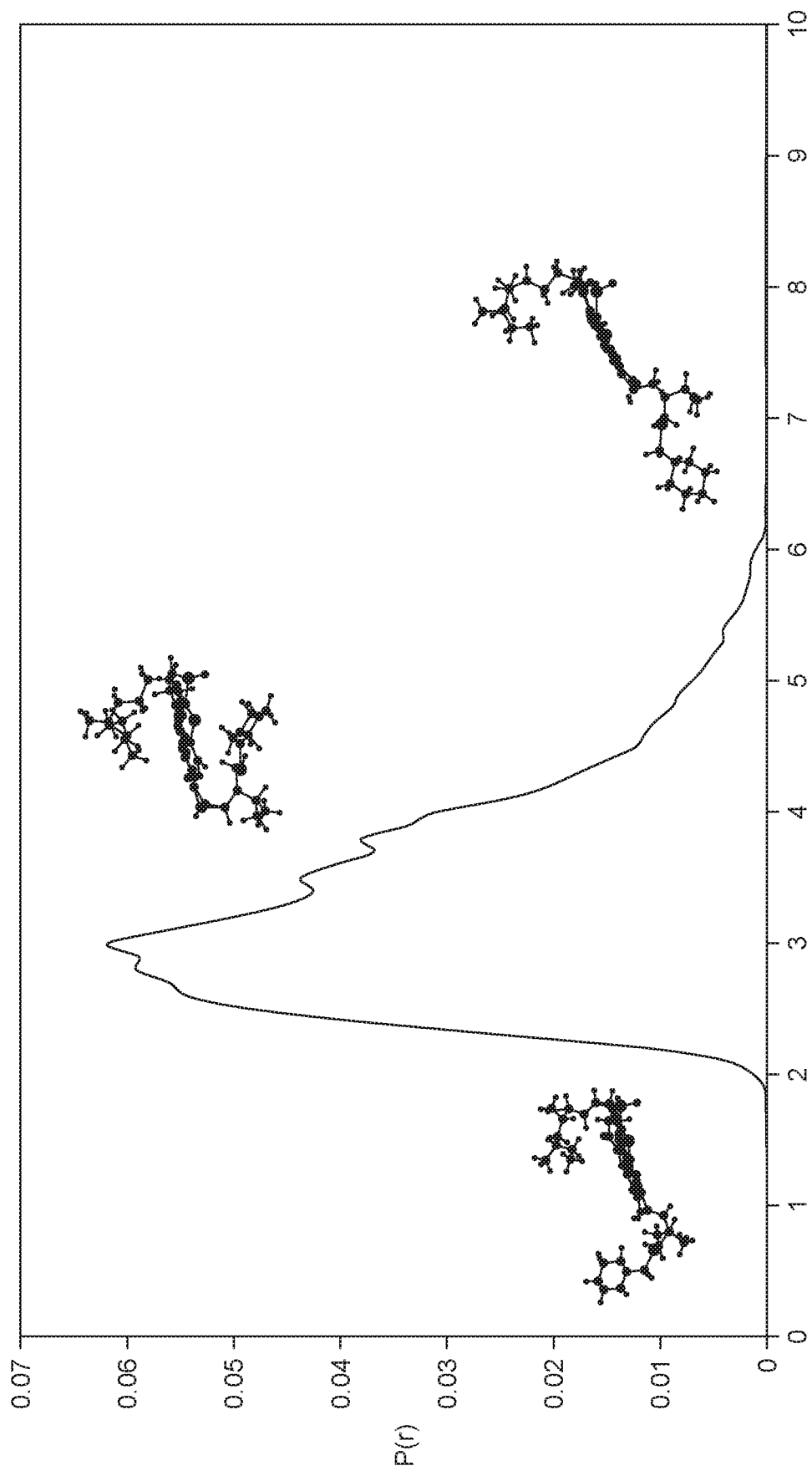
FIG. 13 illustrates the probability distribution for radius of gyrations of alternative conformations for a Canadian asphaltene obtained from NVT simulations at 573 K.

Single point energy calculations for all three of the selected conformations for each alternative conformation were made using Hartree-Fock theory and 6-31G* basis set. The results are illustrated in FIG. 13. The energies of the proposed molecular structures for the three conformations are shown in Table V.

TABLE V

| Structure | Conformation | Energy (Hartree) |
|---|---|---|
| I | max | −4386.796 |
|  | med | −4386.871 |
|  | min | −4386.850 |
| II | max | −4307.570 |
|  | med | −4307.653 |
|  | min | −4307.619 |
| III | max | −4345.507 |
|  | med | −4345.440 |
|  | min | −4345.479 |
| IV | max | −4345.422 |
|  | med | −4345.433 |
|  | min | −4345.512 |
| V | max | −4345.437 |
|  | med | −4345.474 |
|  | min | −4345.481 |
| VI | max | −4345.470 |
|  | med | −4345.453 |
|  | min | −4345.461 |
| VII | max | −4346.665 |
|  | med | −4346.582 |
|  | min | −4346.612 |
| VIII | max | −4346.627 |
|  | med | −4346.607 |
|  | min | −4346.655 |

The structure having the lowest total energy was then selected. For the Canadian oil asphaltene, structure 5 was identified as the lowest energy structure:

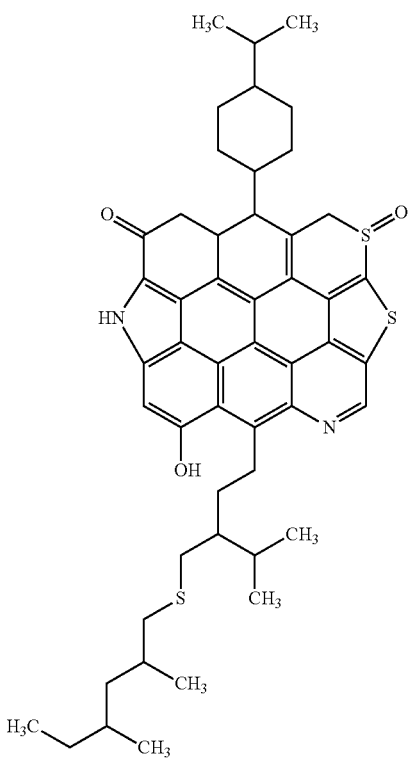 [SMILES: CCC(C)CC(C)CSCC(CCc1c2ncc3sc4c5c6c7c8c9c([nH]c%10cc(O)c1c(c%109)c7c2c35)C(=O)CC8C(C1CCC(C(C)C)CC1)C=6CS4=O)C(C)C]

Using the elucidated structure, potential bonds to be broken during the catalytic reaction were identified. Possible catalysts were then selected from possible catalysts from an inventory containing transition metals. A catalyst system may then be created by combining one or more promoters with the catalyst to enhance efficacy of the catalyst.

Following the procedure of FIG. 2, a zeolite catalyst was modified with the active metals Ni, Mo and Co to make the catalyst more stable under hot water. The catalyst was shown to reduce the viscosity of heavy oil via mild cracking at relatively lower temperatures.

The methods that may be described above or claimed herein may be used to elucidate the structure of any asphaltene extract, including those found in crude oil. The steps of analysis may be performed in any desired suitable order and are not necessarily limited to any sequence described herein or as may be listed in the appended claims.

What is claimed is:

1. A method of catalytically breaking asphaltene macromolecules comprising:
   a. obtaining a sample of a fluid containing the asphaltene macromolecules;
   b. identifying a target structure of the aromatic core of the asphaltene macromolecules in the fluid;
   c. estimating the free energy of the target structure;
   d. identifying aliphatic and functional groups within the asphaltene macromolecules;
   e. approximating the probability of a molecular structure of the target structure and estimating the free energy of the molecular structure;
   f. developing a catalyst system capable of breaking the bonds of a most probable molecule and
   g. breaking down the asphaltene macromolecules into small molecules with the developed catalyst system.

2. The method of claim 1, wherein the fluid is crude oil.
3. The method of claim 1, wherein the functional groups are carbonyls, hydroxyls and sulfoxides.
4. The method of claim 3, wherein the developed catalyst system has a component capable of breaking the bonds of the carbonyl, hydroxyl or sulfoxide functional groups.
5. The method of claim 1, wherein step (b) further comprises determining the percent carbon, hydrogen, nitrogen, oxygen, sulfur, nickel and vanadium in the asphaltene sample.
6. The method of claim 1, further comprising determining the architecture of the asphaltene sample, wherein the architecture is either rosary, island or a combination thereof.
7. The method of claim 1, wherein step (b) further comprises determining the presence and quantity of pyridine, pyrrole, sulfoxide and thiophene in the asphaltene sample.
8. The method of claim 7, wherein the developed catalyst system has a component capable of breaking the bonds of the pyridine, pyrrole, sulfoxide and thiophene.
9. The method of claim 1, wherein the functional groups in the asphaltene sample are determined in step (d) by x-ray photoelectron spectroscopy.
10. The method of claim 1, wherein the aromatic core size of the asphaltene sample is determined in step (b) by Raman spectra.
11. The method of claim 1, wherein step (b) further comprises identifying a type of linkage of a heteroatom in the asphaltene macromolecule.
12. The method of claim 1, further comprising subjecting the asphaltene sample to elemental analysis.
13. The method of claim 1, further comprising assessing the aromatic content, aliphatic content and side chain content of the asphaltene sample.
14. The method of claim 13, further comprising, in conjunction with $^{13}C$, determining the presence of —$CH_3$, —$CH_2$ and —CH in the asphaltene sample by Distortionless Enhancement by Polarization Transfer.
15. The method of claim 1, wherein step (b) further comprises determining chains of the asphaltene sample.
16. The method of claim 1, further comprising determining the molecular weight distribution of the asphaltene sample by Laser Desorption Ionization.
17. A method of catalytically breaking asphaltene macromolecules comprising:
   a. obtaining a most probable molecular structure of the asphaltene macromolecules that is based on target structures of an aromatic core of the asphaltene macromolecules, and that are identified by analytical techniques and a geometric optimization based on a free energy calculation;
   b. performing computational analysis to select a catalyst system from a catalyst inventory, and that is capable of breaking bonds of the most probable molecular structure; and
   c. breaking the bonds of the asphaltene macromolecules with the selected catalyst.
18. A method of breaking bonds in asphaltene macromolecules comprising:
   a. determining a molecular structure of the asphaltene macromolecules based on target structures of an aromatic core of the asphaltene macromolecules;
   b. estimating bond energies of the target structures within the molecular structure;
   c. identifying a catalyst system based on the estimated bond energies; and d. promoting a reaction of the asphaltene macromolecules with the identified catalyst system that breaks down the asphaltene macromolecules.

19. The method of claim 18, further comprising approximating the probability of a molecular structure of the target structures and estimating the free energy of the molecular structure.

20. The method of claim 19, further comprising identifying the most probable structure based on the free energy calculation of the target structure.

* * * * *